United States Patent [19]
Tanokura et al.

[11] Patent Number: 5,523,004
[45] Date of Patent: Jun. 4, 1996

[54] METHOD FOR TREATMENT OF BLOOD USING A BLOOD BAG

[75] Inventors: Nobukazu Tanokura; Yukihiro Ohnaka; Noboru Ishida, all of Shizuoka, Japan

[73] Assignee: Terumo Kabushiki Kaisha, Tokyo, Japan

[21] Appl. No.: 160,829

[22] Filed: Dec. 3, 1993

[30] Foreign Application Priority Data

Dec. 4, 1992 [JP] Japan .................................. 4-350556
Jun. 29, 1993 [JP] Japan .................................. 5-159789

[51] Int. Cl.⁶ .......................... B01D 21/26; A01N 1/02
[52] U.S. Cl. ...................... 210/782; 210/749; 210/767; 210/789; 604/4; 604/5; 604/6; 604/410; 422/1; 422/40; 435/2
[58] Field of Search .................................. 210/749, 767, 210/782, 789; 604/4, 5, 6, 408, 409, 410, 403, 415, 416; 422/1, 40; 435/2

[56] References Cited

U.S. PATENT DOCUMENTS

| | | |
|---|---|---|
| 3,304,977 | 2/1967 | Hammons . |
| 3,985,135 | 10/1976 | Carpenter et al. . |
| 4,379,452 | 4/1983 | DeVries ........................ 604/6 |
| 4,596,657 | 6/1986 | Wisdom ...................... 210/206 |
| 4,810,378 | 3/1989 | Carmen et al. ............. 604/410 |
| 4,863,452 | 9/1989 | Irmiter et al. ............... 604/408 |
| 4,997,577 | 3/1991 | Stewart ....................... 210/767 |
| 5,089,146 | 2/1992 | Carmen et al. ............. 210/782 |
| 5,154,716 | 10/1992 | Bauman et al. ............ 604/410 |

FOREIGN PATENT DOCUMENTS

| | | |
|---|---|---|
| 0267286A1 | 5/1988 | European Pat. Off. . |
| 0474267 | 3/1992 | European Pat. Off. . |
| 0484751 | 5/1992 | European Pat. Off. . |
| 2305991 | 10/1976 | France . |
| 62-039636 | 2/1987 | Japan . |
| 3123630 | 5/1991 | Japan . |
| 584071 | 4/1993 | Japan . |
| 2238055 | 5/1991 | United Kingdom . |
| WO82/01477 | 5/1982 | WIPO . |

*Primary Examiner*—John Kim
*Attorney, Agent, or Firm*—Burns, Doane, Swecker & Mathis

[57] ABSTRACT

A composite of interconnected bags comprises a blood collecting bag, a preserving liquid bag, and a blood plasma bag. The interior of the bag body of the blood collecting bag is divided by a partition strip into an empty space and an empty space of the shape of a strip, with the two empty spaces mutually communicating near the end part of the partition strip. The blood collected in the blood collecting bag is centrifuged. The upper layer of blood plasma resulting from the centrifugation is discharged via a tube to the blood plasma bag. Then, the erythrocyte preserving liquid in the preserving liquid bag is advanced through the tube, the empty space, and a connecting part and added upwardly from below to the concentrated erythrocyte left behind the empty space. The erythrocyte preserving liquid, without being stirred, is allowed to ascend and mingle with the concentrated erythrocyte with the elapse of time. Thus, the present invention provides a erythrocyte preparation excellent in quality and fee from occurrence of floccules.

22 Claims, 14 Drawing Sheets

METHOD FOR TREATMENT OF BLOOD USING A BLOOD BAG

BACKGROUND OF THE INVENTION

1. Field of the Invention

This invention relates to a body fluid bag and a method for the treatment of blood. More particularly, it relates to a body fluid bag for storing a body liquid such as blood and marrow liquid and being subjected to centrifugal operation, a method for ideally adding for admixture the preserved solution of erythrocyte remaining after the separation of concentrated erythrocyte component from blood to the concentrated erythrocyte component.

2. Description of the Prior Art

In the operation of blood transfusion, the system relying on a procedure which comprises separating the blood extracted from donors into blood components as by means of centrifugation and using for the transfusion only those of the separated blood components which are necessary for particular donees is now prevailing for the sake of promoting effective use of blood and lessening the burden on the part of donors. This componential transfusion of recent introduction has been serving the purpose of permitting effective use of blood as compared with the conventional whole blood transfusion.

In the componential transfusion just mentioned, the closed and sterilized blood bags of the triple type or quadruple type illustrated in FIG. 11 and FIG. 12 are used most widely. These blood bags 5, 6 generally comprise a relatively large parent bag (blood collection bag) 121 serving to collect whole blood and having an anticoagulant liquid for hindering coagulation of blood enclosed therein, one or two daughter bags 123, 124 connected to the parent bag 121 through the medium of a connecting tube 122 provided above the parent bag 121 and adapted to transfer and seal in a blood component, and a preserving liquid bag 125 connected to the parent bag 121 through the medium of the connecting tube 122 provided above the parent bag 121 and having enclosed therein a erytocyte preserving liquid to be added, subsequently to the separation of blood components, to the erythrocyte in the parent bag 121 and enabled to permit safe preservation of erythrocyte for a long time.

After the blood has been collected in the blood bag of this construction from a donor, the whole blood is generally stored in the unmodified form therein or it is separated into blood components and stored as such in preparation for actual use. The separation is effected by sedimentation or centrifugation. As a result, the blood is separated into an upper layer of blood plasma and a lower layer of erythrocyte or into an upper layer of blood plasma, an intermediate layer of buffy coat (a thin soft film layer containing white blood corpuscles and blood platelets), and a lower layer of erythrocyte.

In any event, the erythrocyte is are left in the parent bag 121. The erythrocyte thus separated are combined with the erythrocyte preserving liquid when this liquid is transferred from the preserving liquid bag 125 via the connecting tube 122 to the parent bag 121. In the parent bag 121, the resultant blend is stored as a red blood preparation useful as for transfusion.

In the conventional method for the treatment of blood which is operated as described above, however, the erythrocyte preserving liquid is destined to be added downwardly to the parent bag from the upper side thereof. The erythrocyte preserving liquid has a lower specific gravity than the erythrocyte and the erythrocyte is are pressed in a highly densified state against the bottom part of the parent bag by the centrifugal force exerted thereon in the process of centrifugal separation. The erythrocyte preserving liquid in its unmodified form, therefore, cannot be thoroughly mixed with the erythrocyte and, on being admixed therewith somehow or other, often gives rise to floccules (such as of leukocyte, blood platelets, and fibrins), and inevitably entails the problems of degrading the quality of the erythrocyte preparation to be eventually obtained. To preclude this problem, therefore, the conventional method has been required to subject the erythrocyte to the action of stirring during or immediately after the addition of the erythrocyte preserving liquid.

In order to improve the defects of such bag, a blood bag provided a zonal partition part for dividing an interior of the bag body into two spaces between two ports formed at an upper portion of the bag body (EP-A-O 484 751).

The partition part of the blood bag is obtained by sealing (melting) resin sheets which constitute the bag body from upper portion of the bag body to a half portion of the bag body with a long zonal shape parallely with a side portion of the bag body, but the lower end portion is a cut shape (See FIG. 2) and the width of the partition part is constant, so sealing strength is low. Therefore, there are defects that when the blood bag is subjected to centrifugation after filling blood into the blood bag, inner pressure of lower portion of the blood bag of the blood bag increases, and expands, so if stress concentrates to lower end region of the partition part, pealing or crack generates at this portion, and finally the bag body sometimes explodes.

Further, the distance between a center of the partition part of the blood bag and side portion of the bag body near the center, i.e., the width of a channel wherein blood goes through is defined not more than 7 mm, so there are defects that the channel is apt to blockade by deformation of the side portion of the bag under the condition of expansion of the blood bag after centrifugation, and even if such blockade does not generate, discharging rate of erythrocyte is low because of too narrow width of the channel.

Furthermore, in the blood bag, two valves provided at an upper portion of the bag and connected with tubes for discharging plasma and erythrocyte project in two spaces divided by the partition part, and the operation for opening the valves is carried out by pinching the valves together with the bag, so there are problems that vibration (liquid fluidization) is transferred and boundaries of each separated layers is disordered, and as a result, recovery ratio of erythrocyte decreases and mixing ratio of leukocyte in the plasma increases.

Therefore, an object of the present invention is to provide a body fluid bag which is suitable for centrifugal separation, has no trouble about breakage of the partition part, is easy to produce and to handle, can make discharge a separated component without using a specific device, can make obtain the same or more recovery ratio or separation ratio of the separated component compared with a conventional method even if recovery of the separated component is carried out by using a conventional simple device, and can make sufficient discharging rate of the separated component.

The present invention, conceived in the urge to protect the conventional method of blood treatment against the problem of frequently entailing the occurrence of floccules in the erythrocyte preparation, has as an object thereof the provision of a method for the treatment of blood which can produce a erythrocyte preparation of high quality without entailing the occurrence of floccules.

SUMMARY OF THE INVENTION

These objects can be attained by the present invention of the following (1). Further, the following (2) to (15) are preferable (1) A body fluid bag which comprises having a pouchy bag body for storing blood, a partition strip extended inside the bag body from one end part for partitioning to at least two empty spaces, and a first and a second tubes connected to one end part of the bag body as opposed to each other across the partition strip, each empty spaces partitioned by said partition strip being communicated with each other near the other end part of the partition strip, the other end part of the partition strip being formed a curved shape and a curvature radius thereof R satisfying the following formula, when a partition width being H:

$$0.75H \leq R$$

the first tube being communicated with one empty space partitioned by the partition strip part when the fluid flowing, and the second tube being communicated with the other empty space partitioned by the partition strip part when the fluid flowing.

(2) A body fluid bag according to the aspect (1), wherein the other end part of the partition strip is located near an end part opposite to the end part to which the first and second tubes of the bag body are connected.

(3) A body fluid bag according to the aspect (1) or (2), wherein the partition strip is provided at the other end thereof with a land part having the shape a circle, an ellipse, or a waterdrop.

(4) A body fluid bag according to any of the aspects (1) to (3), wherein at least one of the empty spaces divided by the partition strip has the shape of a ribbon.

(5) A body fluid bag according to the aspect (4), wherein the strip empty space is formed along with a side part of the bag body.

(6) A body fluid bag according to the aspect (4) or (5), wherein the minimum width of the strip empty space is 7 to 13 mm.

(7) A body fluid bag according to the aspect (4) or (5), wherein the minimum width a of the strip empty space satisfies the following formula, when a distance f between a center line of the bag body and an end part of apposite side to the partition strip part of the strip empty space:

$$0.05 \leq a/f \leq 0.30$$

(8) A body fluid bag according to any one of the aspects (4) to (7), wherein the width of the strip empty space at the other end part region of the partition strip part increases gradually to a direction of the end part of the partition strip.

(9) A body fluid bag according to the aspect (8), wherein the minimum width a of the strip empty space and the width b of the strip empty space at the other end part region of the partition strip part satisfy the following formula.

$$1.25 \leq b/a \leq 2$$

(10) A body fluid bag according to any one of the aspects (1) to (9), wherein the with H of the partition strip is 1 to 15 mm.

(11) A body fluid bag according to any one of the aspects (1) to (10), wherein the bag body has a plurality of the partition part and the inside of the bag body is partitioned to at least three empty spaces.

(12) A body fluid bag according to any one of the aspects (1) to (11), wherein the partition strip is formed by adhesion or heat melting of the sheet materials which constitute the bag body.

(13) A body fluid bag according to any one of the aspects (1) to (12), wherein the first and the second tubes are for discharging each different components to outside of the bag body.

(14) A body fluid bag according to any one of the aspects (1) to (13), wherein a tube for introducing the body fluid into the bag body is connected with an end part of the bag body.

(15) A body fluid bag according to any of the aspects (1) to (14), wherein other bag body is connected with at least one of the first and the second tubes.

This object is accomplished by the following aspects (16) and (17) of this invention. The following aspects (18) through (27) of this invention are likewise preferable for the accomplishment of the object.

(6) A method for the treatment of blood by the use of a blood bag comprising a pouchy bag body for storing blood, a partition strip extended inside the bag body from one end part to the other end part of the bag body, and first and second tubes connected to one end part of the bag body as opposed to each other across the partition strip, with the interior of the bag body partitioned by the partition strip into at least two empty spaces communicating with each other near the other end part of the partition strip, which method is characterized by centrifuging the blood collected in the blood bag with one end part of the bag body held on the upper side thereby separating the blood into an upper layer of blood plasma and a lower layer of concentrated erythrocyte, discharging the blood plasma to the exterior of the bag body via the first tube, and then transferring the erythrocyte preserving liquid to the interior of the bag body via the second tube thereby effecting addition of the erythrocyte preserving liquid to the concentrated erythrocyte.

(17) A method for the treatment of blood by the use of a blood bag comprising a pouchy bag body for storing blood, a partition strip extended inside the bag body from one end part to the other end part of the bag body, and first and second tubes connected to one end part of the bag body as opposed to each other across the partition strip, with the interior of the bag body partitioned by the partition strip into at least two empty spaces communicating with each other near the other end part of the partition strip, which method is characterized by centrifuging the blood collected in the blood bag with one end part of the bag body held on the upper side thereby separating the blood into an upper layer of blood plasma, an intermediate layer of leukocyte, and a lower layer of concentrated erythrocyte, discharging the blood plasma and subsequently the leukocyte to the exterior of the bag body via the first tube and then transferring the erythrocyte preserving liquid to the interior of the bag body via the second tube thereby effecting addition of the erythrocyte preserving liquid to the concentrated erythrocyte.

(18) A method according to the aspect (16) or (17), wherein the other end part of the partition strip is located near an end part opposite to the end part to which the first and second tubes of the bag body are connected.

(19) A method according to any of the aspects (16) to (18), wherein the partition strip is provided at the other end thereof with a land part having the shape a circle, an ellipse, or a waterdrop.

(20) A method according to any of the aspects (16) to (19), wherein at least one of the empty spaces divided by the partition strip has the shape of a ribbon.

(21) A method according to any of the aspects (16) to (20), wherein the partition strip is has been obtained by the adhesion or fusion of the same sheet material as that used for the bag body.

(22) A method according to any of the aspects (16) to (21), wherein a third tube for introducing the blood into the bag body is connected to one end part of the bag body.

(23) A method according to any of the aspects (16) to (22), wherein the first and second tubes are severally provided with connecting members serving to connect the tubes to the bag body.

(24) A method according to the aspect (23), wherein the connecting members severally incorporate therein blocking members which normally impede communication of the bag body with the first and second tubes and, on being fractured, permit the communication.

(25) A method according to the aspect (24), wherein the blocking members are provided outside the bag body.

(26) A method according to any of the aspects (16) to (25), wherein the preserving liquid bag containing the erythrocyte preserving liquid is connected to the second tube.

(27) A method according to any of the aspects (16) to (26), wherein another bag body is connected to the first tube.

EXPLANATION OF THE PREFERRED EMBODIMENT

In the method of this invention for the treatment of blood, since the erythrocyte preserving liquid is added to the blood bag upwardly from the lower side thereof unlike the conventional method which makes this addition downwardly from the upper part of the blood bag, the erythrocyte preserving liquid which has a lower specific gravity than the erythrocyte ascends the mass of erythrocyte while diffusing therein and the erythrocyte of a higher specific gravity gradually descend the mass of the erythrocyte preserving liquid. Thus, the erythrocyte preserving liquid and the erythrocyte is thoroughly stirred naturally without requiring any special treatment.

In the conventional blood bag, the erythrocyte preserving liquid can be added upwardly to the bag from the lower side thereof by keeping the bag set upside down. In the present invention, however, since the first and second tubes are connected to one end part of the blood bag, the series of operations such as centrifugal treatment of blood, separation of blood components, and addition of the erythrocyte preserving liquid can be performed with the one end part of the blood bag kept on the upper side. Thus, the time and labor otherwise required for the extra work of reversing the blood bag can be obviated.

Further, since the first and second tubes are connected to one end part of the blood bag, these tubes can be so constructed as to avoid thrusting into the bottom part of the bag. When the blood bag is to be inserted in a centrifugal cup in preparation for the centrifugal treatment, therefore, these tubes neither impede the insertion nor cause the bag to sustain breakage due to the otherwise possible occurrence of a dead space inside the centrifugal cup.

Now, this invention will be described below with reference to specific embodiments thereof.

Figure 1:
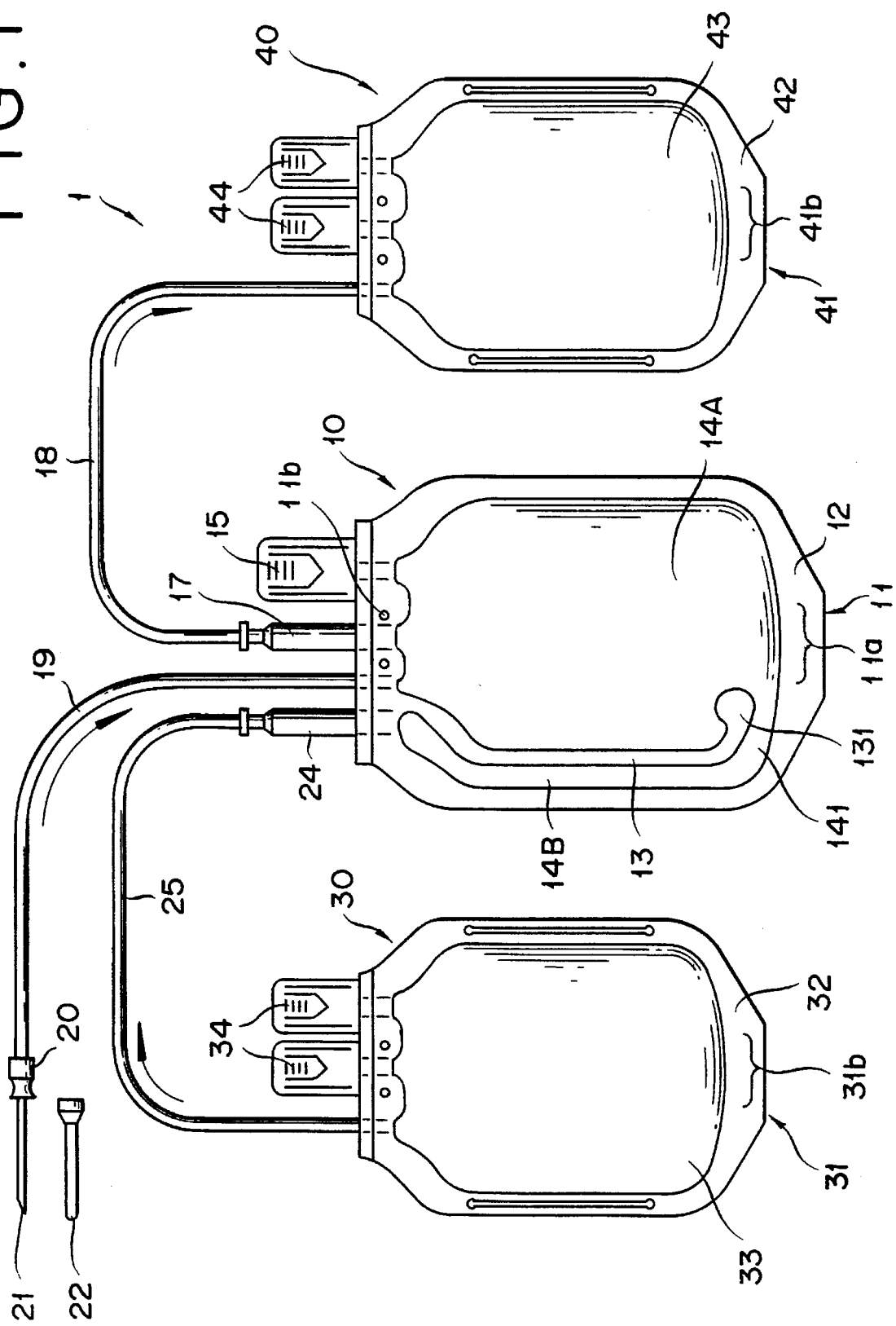
FIG. 1 is a plan view illustrating an embodiment of the construction of a blood bag to be used for this invention.

FIG. 1 is a plan view illustrating one embodiment of the construction of a composite obtained by connecting one blood bag to another blood bag through the medium of a tube and arranged for use in the method of this invention for the treatment of blood. As illustrated in this diagram, a composite 1 of interconnected bags is a triple bag having a blood collecting bag, a blood plasma bag, and a erythrocyte preserving liquid bag interconnected with tubes.

A blood collecting bag 10 positioned at the center of the diagram of FIG. 1 comprises a bag body 11 formed in the shape of a pouch by superposing a pair of identically cut pieces of a sheet material made of a resin which will be more specifically described hereinafter and possessed of flexibility and fusing (by thermal fusion or high-frequency fusion) or adhesively joining seal parts 12 along the edge regions of the superposed pieces of the sheet material.

The interior of this bag body 11 is partitioned with a partition strip 13 into two empty spaces 14A and 14B. The empty space 14A occupies the greater part of the interior of the bag body 11 and the empty space 14B is in the shape of a trip formed along the lateral part of the bag body 11. The empty space 14B, as described hereinafter, functions as a flow path for introducing the erythrocyte preserving liquid from the interior of a preserving liquid bag 30 into the bag body 11. When the empty space 14B is formed in the shape of a strip (a thin column in an inflated state), the flow of the erythrocyte preserving liquid inside the empty space 14B toward the lower part (bottom part) side of the bag body 11 proceeds smoothly and does not easily entail backflow.

These two empty spaces 14A and 14B, as illustrated in FIG. 1, communicate with each other near the lower end part (end part 131) of the partition strip 13, namely near the bottom part (communicating part 141) of the bag body 11.

The partition strip 13 is connected in the upper end thereof to the seal part 12. Preferably, this partition strip 13 is formed simultaneously with the seal part 12 by fusing (by thermal fusion or high-frequency fusion, for example) or adhesively joining the same sheet material as that used for the bag body 11. By this method, the partition strip 13 can be easily formed without entailing any addition to the number of steps in the process of manufacture.

The width of the partition strip 13 is not critical. When the partition strip 13 is formed by fusing or adhesively joining the sheet material, however, this width is preferable to fall in the approximate range of 1 to 15 mm, preferably 2 to 10 mm, on an average in consideration of the peel strength.

Though the shape of the end part 131 of the partition strip 13 is not critical, the end part 131 is preferable to have a curved shape. The curve is preferable to satisfy the relation $0.75H \leq R$, preferably $H \leq R$, wherein R is the radius of curvature and H is the width of the partition strip 13 (the average of the width of the partition strip 13 except for the end part 131). When the inner pressure of the blood collecting bag 10 increases as when the bag is subjected to the centrifugal treatment, the end part 131 of the partition strip 13 is liable to fall a victim to concentrated stress. So long as the relation mentioned above is satisfied, however, the end part 131 of the partition strip 13 is prevented from sustaining a crack and consequently the bag body 11 is precluded from fracturing in consequence of a crack in the end part 131.

For the purpose of satisfying the relation mentioned above, the end part 131 is preferable to be provided with a land part which, as illustrated in the diagram, has the shape of a circle, an ellipse, a waterdrop, or a suitable combination thereof. When the contour of this land part happens to be such that the radius of curvature R thereof lacks constancy as in the case of an ellipse, for example, the minimum numerical value of the radius of curvature R is preferable to satisfy the relation mentioned above.

Figure 2:
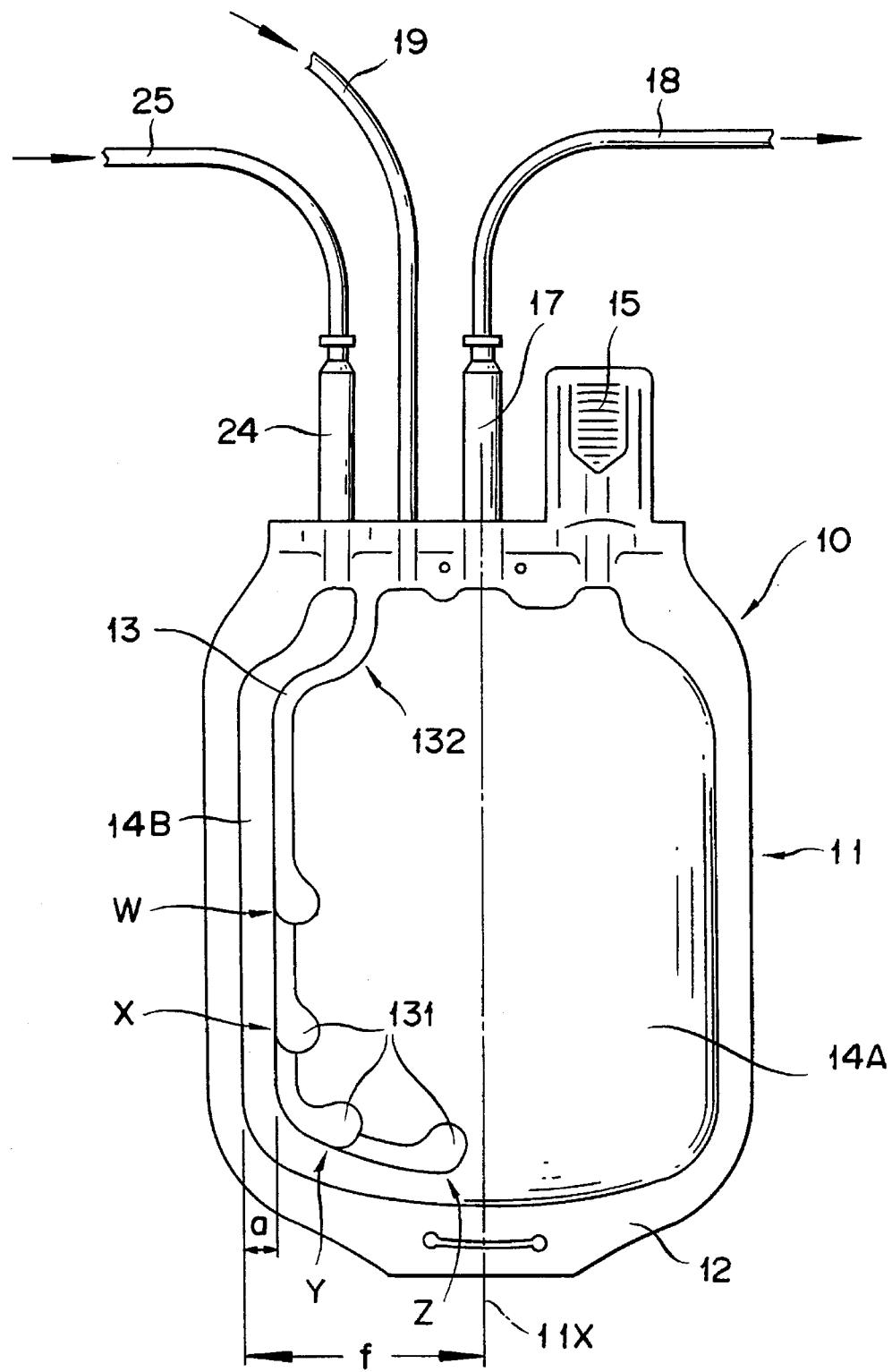
FIG. 2 is a plan view illustrating the position of the end part of a partition strip in the blood bag shown in FIG. 1.

FIG. 2 is a plan view illustrating the position of the end part of the partition strip 13 in the blood collecting bag 10. An end part 131 of the partition strip 13 may assume any of the positions W, X, Y, and Z indicated in FIG. 2. It may otherwise fall anywhere between these positions.

The position indicated by W in FIG. 2 is slightly below the boundary between the lower layer of erythrocyte and the upper layer of blood plasma which have been separated by the centrifugation which has been performed on the blood stored in the bag body 11 of the blood collecting bag 10 as will be described specifically hereinbelow. The position indicated by Z is on the lowest possible level, namely near the center of the bottom part of the bag body 11.

It is particularly preferable for the end part 131 of the partition strip 13 to assume any of the positions falling in the range from the position X to the position Z, preferably in the range from the position X to the position Y. As a result of this deliberate location, the insertion of the blood collecting bag 10 into the centrifugal cup can be facilitated, the possibility of the bag sustaining fracture by the impact of the end part 131 during the operation of centrifugal separation can be further diminished, the amount of leukocyte suffered to leak into the separated layer of erythrocyte can be notably decreased, and the ratio of recovery of erythrocyte can be improved.

The seal part 12 of the partition strip 13 is preferable to be provided in the vicinity thereof with an upper curved part 132 which is curved so as to describe an arc in the direction of the bag body side as illustrated. The radius of curvature R' of the upper curved part 132 is preferable to satisfy the relation 10 mm$\leq$R', preferably 15 mm$\leq$R', from the point of view of preventing exfoliation of the upper curved part 132.

When the empty space 14B is formed in the shape of a strip as illustrated in the diagram, the minimum numerical value a of the width of this empty space 14B is preferable to satisfy the relation $2c<a<5c$ wherein c is the inside diameter of a tube 25. Specifically, the minimum width a is preferable to be in the approximate range of 4 to 18 mm. If the minimum width a of the empty space 14B is less than 4 mm, the empty space 14B tends to be blocked by the deformation which occurs on the bag body 11 side when the bag body 11 is inflated after the operation of centrifugal separation or, even in the absence of this blockage, the width of the empty space 14B is so narrow as to slow down the speed of the inflow of the erythrocyte preserving liquid into the bag body 11 which will be described specifically hereinbelow. Conversely, if this minimum width a exceeds 18 mm, the ratio of recovery of erythrocyte (the ratio of removal of leukocyte mingling with erythrocyte) is lowered.

For the same reason as described above, the minimum numerical value a of the width of the empty space 14B is preferable to satisfy the relation $0.05 \leq a/f \leq 0.30$, preferably $0.1 \leq a/f \leq 0.23$, wherein f is a distance between the center line 11x of the bag body 11 and a boundary of the empty space 14B with the seal part 12 (FIG. 2).

Incidentally, the width of the empty space 14B does not need to be constant throughout the entire length of this empty space 14B but may be gradually decreased or increased from the upper to the lower part of the bag body 11.

Figure 3:
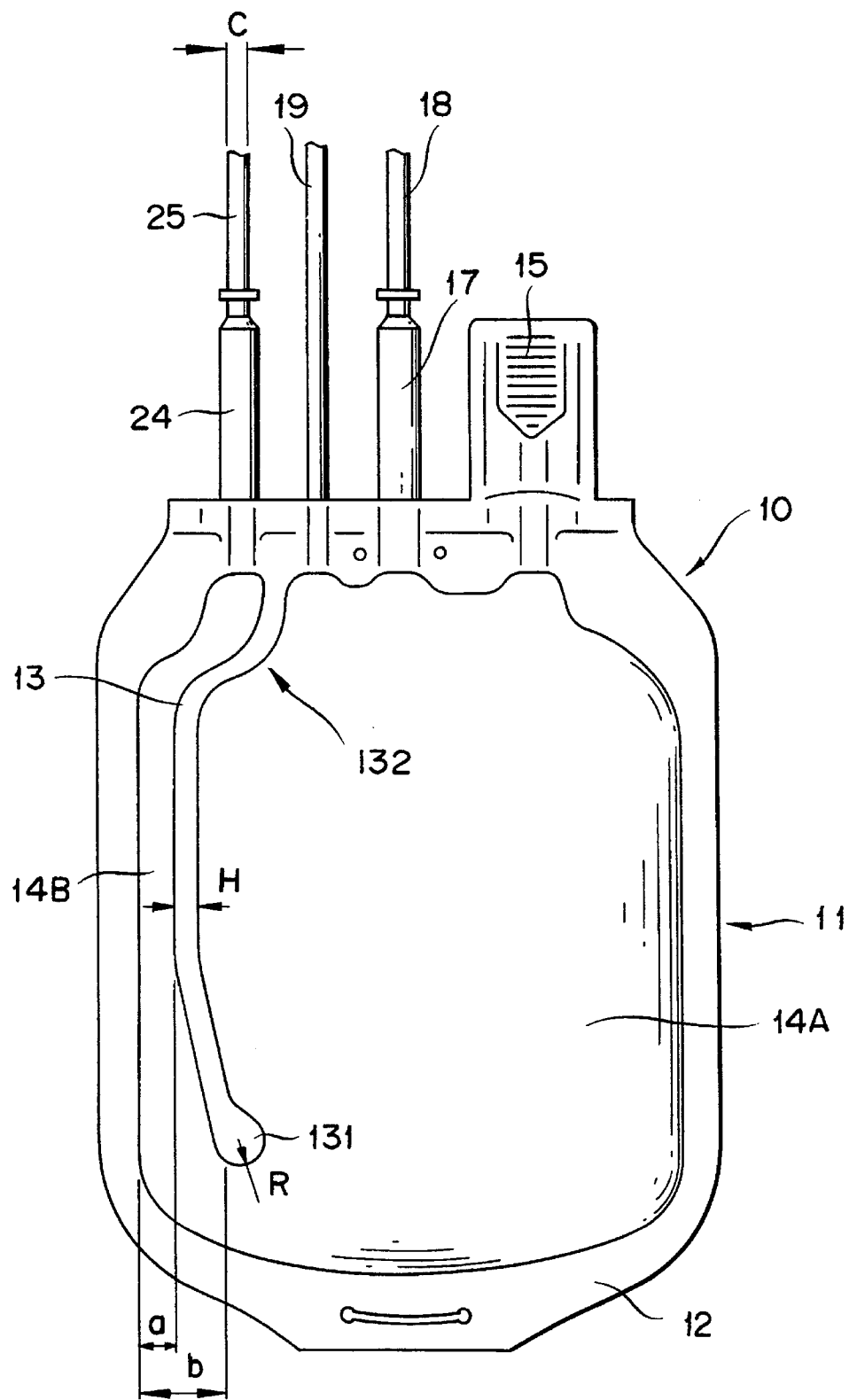
FIG. 3 is a plan view illustrating embodiment example of the construction of the blood bag (blood collecting bag) to be used for this invention.

FIG. 3 is a plan view illustrating another embodiment of the construction of the blood collecting bag 10. The blood collecting bag 10 shown in this diagram is so constructed that the width of the empty space 14B is continuously increased from a position falling somewhere in the length of the partition strip 13, namely in the vicinity of the position W shown in FIG. 2 to the end part 131 of the partition strip 13. By this arrangement, the addition of the erythrocyte preserving liquid to erythrocyte and the mixture thereof can be ideally effected.

In the case of this arrangement, the minimum numerical value a of the empty space 14B and the maximum numerical value b (the width of the empty space 14B at the end part 131) is preferable to satisfy the relation $1.25 \leq b/a \leq 2$. When the ratio falls in this range, the addition of the erythrocyte preserving liquid to the erythrocyte and the mixture thereof are accomplished more advantageously.

Though the ratio of the inner volumes of the empty spaces 14A and 14B is not particularly limited, the inner volume of the empty space 14B is preferable to be less than 5%, particularly to be in the approximate range of 0.6 to 4.0%, based on the total inner volume of the bag body. When this range is satisfied, the amount of blood suffered to flow in the empty space 14B is conspicuously decreased, the amount of such other blood components as blood plasma than erythrocyte suffered to flow into the empty space 14B is likewise decreased, and the ratio of recovery of erythrocyte and the ratio of removal of leukocyte from erythrocyte are further increased. Moreover, the erythrocyte preserving liquid which has been transferred into the bag body 11 is allowed to flow substantially wholly into the empty space 14A. Thus, the operation of this invention can be manifested ideally.

The bag body 11 is provided on the upper part (the upper end part in the bearings of the diagram) thereof with a discharge port 15 for transfusion sealed openably with a peel tab and a connecting member 17 for connection to a blood plasma bag 40. Besides, the bag body 11 has connected thereto one end of a tube 19 which is flexible and is adapted to introduce the collected blood. The discharge port 15, the connecting member 17, and the tube 19 communicate with the empty space 14A.

To the connecting member 17 is connected one end of a tube 18 which is flexible. The tube 18 is connected at the other end thereof to the upper part of the blood plasma bag 40 which will be specifically described hereinbelow.

A blood collecting needle 21 is attached via a hub 20 to the other end of the tube 19. A cap 22 encasing the blood collecting needle 21 is attached to the hub 20.

On the left side in the bearings of the diagram of the tube 19 on the bag body 11, a connecting member 24 similar to the connecting member 17 mentioned above is disposed so as to be connected to the erythrocyte bag 30. This connecting member 24 communicates with the empty space 14B. Further, to the connecting member 24 is connected one end of a tube 25 which has flexibility. The tube 25 is connected at the other end thereof to the upper part of the preserving liquid bag 30.

The connecting members 17 and 24 are preferable each to be provided with a sealing member which blocks a flow path thereof in a non-fractured state and opens the flow path in a fractured state. Examples of the construction of this sealing member will be cited hereinbelow.

These connecting members 17 and 24 are so disposed as to protrude outwardly from the bag body 11 and not to thrust into the empty spaces 14A and 14B. They contribute to exaltation of the yield of separation of blood components by eliminating the possibility that the boundaries of the layers of blood components separated in the bag by centrifugal treatment will be disturbed by the otherwise inevitable vibration (movement of the liquid) generated while the connecting members 17 and 24 are opened.

This invention allows the tubes 18 and 25 to be suitably closed or opened by means of clamps, for example, instead of such connecting members 17, 24 as mentioned above.

The preserving liquid bag 30 positioned on the left side in the bearings of FIG. 1 comprises a pouchy bag body 31 which is obtained by superposing matched pieces of a sheet material formed of a resin to be described specifically afterward and possessed of flexibility and fusing (by thermal fusion or high-frequency fusion, for example) or adhesively joining seal parts 32 of the superposed pieces along the periphery thereof.

In the inside part of the bag body 31 which is enclosed with the seal parts 32, there is formed a preserving liquid storing part 33 for storing the erythrocyte preserving liquid which is destined to be added to the concentrated erythrocyte separated from the blood in the blood collecting bag 1.

Two transfusion discharge ports 34 and 34 sealed openably with a peel tab are formed on the preserving liquid bag 30. To the side of the discharge ports 34, the tube 25 communicating with the preserving liquid storing part 33 is connected at one end thereof. Owing to this arrangement, the empty space 14B of the blood collecting bag 10 and the preserving liquid storing part 33 of the preserving liquid bag 30 are allowed to communicate with each other via the tube 25 when the flow path of the connecting member 24 is opened. This invention permits omission of the discharge ports 34.

The blood plasma bag 40 positioned on the right side in the bearings of FIG. 1 comprises a pouchy bag body 41 which is obtained by superposing matched pieces of a sheet material formed of a resin to be described specifically hereinbelow and possessed of flexibility and fusing (by thermal fusion or high-frequency fusion, for example) or adhesively joining seal parts of the superposed pieces along the periphery thereof.

In the inside part of the bag body 41 enclosed with the seal members 42, there is formed a blood plasma storing part 43 which serves to store the blood plasma separated from the blood in the blood collecting bag 1.

On the blood plasma bag 40, two transfusion discharge ports 44 and 44 each sealed openably with a peel tab are formed. To the side of the discharge ports 44, the aforementioned flexible tube 18 which communicates with the blood plasma storing part 43 is connected at one end thereof. Owing to this arrangement, the empty space 14A of the blood collecting bag 10 and the blood plasma storing part 43 of the blood plasma bag 40 are allowed to communicate with each other through the medium of the tube 18 when the flow path of the connecting member 17 is opened.

In the bottom parts of the bags 10, 30, and 40, slits which are to be used for the purpose of enabling these bags to be hung in the course of transfusion from the hanger of a transfusion stand or from the hook of an automatic blood separating device. Further, in the upper part of the blood collecting bag 10, a hole 11b adapted to attach the bag 10 to the automatic blood separating device to be described specifically hereinbelow.

In the composite 1 of interconnected bags illustrated in FIG. 1, the sheet material of which the bags body of the bags 10, 30, and 40 are formed is ideally made of flexible polyvinyl chloride.

The plasticizers which are effectively usable in this flexible polyvinyl chloride include di(ethylhexyl) phthalate (DEHP) and di-(n-decyl) phthalate (DnDP), for example. The content of such a plasticizer in the polyvinyl chloride is preferable to be in the approximate range of 30 to 70 parts by weight, based on 100 parts by weight of polyvinyl chloride.

The other substances which are effectively usable for the sheet material of the bags 10, 30, and 40 are polyolefins, i.e. the products of homopolymerization or copolymerization of such olefins or diolefins as ethylene, propylene, butadiene, and isoprene. As typical examples, polyethylene, polypropylene, ethylene-vinyl acetate copolymer (EVA), polymer blends formed between EVA and various thermoplastic elastomers, and arbitrary combinations thereof may be cited. Besides, such polyesters as polyethylene terephthalate (PET), polybutylene terephthalate (PBT), and poly-1,4-cyclohexane dimethyl terephthalate (PCHT) and polyvinylidene chloride are also usable.

The thickness of the sheet material of which the bags 10, 30, and 40 are formed is decided in consideration of such factors as the permeability to oxygen gas, carbon dioxide gas, and other similar gases and the strength required to withstand the impact of the operation of centrifugal separation. Generally, the thickness of the sheet material of the blood collecting bag 10 is preferable to be in the approximate range of 0.2 to 1.0 mm, preferably 0.3 to 0.5 mm, though dependent on the particular substance of the sheet material. The thicknesses of the sheet material for the preserving liquid bag 30 and the blood plasma bag 40 are severally preferable to be in the approximate range of 0.2 to 0.7 mm, preferably 0.3 to 0.5 mm.

Though the inner volume of the blood collecting bag 10 has no particular restriction, it must conform to the amount of blood to be collected. For the blood collecting bags which prevail in Japan, this inner volume is in the approximate range of 200 to 400 ml. For those blood collecting bags which prevail in foreign countries, the inner volume is in the approximate range of 350 to 600 ml.

Though the inner volumes of the preserving liquid bag 30 and the blood plasma bag 40 have no particular restriction, those of the bags prevailing in Japan are preferable to be in the approximate range of 100 to 400 ml, preferably 150 to 300 ml and those of the bags prevailing in foreign countries in the approximate range of 150 to 600 ml, preferably 200 to 450 ml.

In the composite 1 of interconnected bags illustrated in FIG. 1, the materials which are effectively usable for the formation of the tubes 18, 19, and 25 and tubes 62, 63, 81, and 83 to be described specifically hereinbelow include flexible polyvinyl chloride, polyethylene, polypropylene, and such polyesters as PET and PBT, ethylene-vinyl acetate copolymer, polyurethane, and such thermoplastic elastomers as polyester elastomer and styrene-butadiene-styrene copolymer, for example. Among other materials mentioned above, polyvinyl chloride proves to be particularly preferable. This is because the tubes made of flexible polyvinyl chloride abound in flexibility and softness enough to be handled easily and blocked readily as with clamps and joined ideally to the relevant bags body 11, 31, and 41. The kind of the plasticizer to be used for the tubes and the content of the plasticizer in the tubes are not particularly restricted.

The blood collecting bag 10 is preferable to have a suitable anticoagulant agent contained in advance therein. Generally, the anticoagulant agent is liquid. As typical examples of the anticoagulant agent, ACD-A liquid, CPD liquid, CPDA-1 liquid, and heparin sodium liquid may be cited. The components of these liquids are shown in Table 1 given below.

TABLE 1

| Anticoagulant agent | Components (g/100 ml × 100) | |
|---|---|---|
| ACD-A liquid | Sodium citrate | 2.20 W/V % |
| | Citric acid | 0.80 W/V % |
| | Glucose | 2.20 W/V % |
| CPD liquid | Sodium citrate | 2.63 W/V % |
| | Citric acid | 0.327 W/V % |
| | Glucose | 2.32 W/V % |
| | Monosodium phosphate | 0.251 W/V % |
| CPDA-1 liquid | Sodium citrate | 2.63 W/V % |
| | Citric acid | 0.327 W/V % |
| | Glucose | 2.9 W/V % |
| | Monosodium phosphate | 0.251 W/V % |
| | Adenine | 0.0275 W/V % |
| Heparin | Sodium chloride | 0.9 W/V % |
| | Heparin sodium | 500 U/15 ml |

The adequate amounts of such anticoagulant agents to be used are about 15 ml in the case of the ACD-A liquid and the heparin sodium liquid and about 14 ml in the case of the CPD liquid and the CPDA-1 liquid, based on 100 ml of the whole human blood.

The erythrocyte preserving liquid to be used in the present invention is placed in the preserving liquid bag 30. As typical examples of the erythrocyte liquid, the S.A.G.M liquid (an aqueous solution containing 0.877 W/V % of sodium chloride, 0.0169 W/V % of adenine, 0.818 W/V % of glucose, and 0.525 W/V % of D-mannitol), the OPTISOL liquid, the ADSOL liquid, and the MPA liquid may be cited. The components of these liquids are shown in Table 2 below.

TABLE 2

| Erythrocyte preserving liquid | Components (g/100 ml × 100) | |
|---|---|---|
| S.A.G.M. liquid | Sodium chloride | 0.877 W/V % |
| | Adenine | 0.17 W/V % |
| | Glucose monohydrate | 0.900 W/V % |
| | Mannitol | 0.525 W/V % |
| OPTISOL liquid | Sodium chloride | 0.900 W/V % |
| | Adenine | 0.27 W/V % |
| | Glucose monohydrate | 2.000 W/V % |
| | Mannitol | 0.750 W/V % |
| ADSOL liquid | Sodium chloride | 0.877 W/V % |
| | Adenine | 0.30 W/V % |
| | Glucose monohydrate | 0.900 W/V % |
| | Mannitol | 0.525 W/V % |
| MAP liquid | Sodium chloride | 0.552 W/V % |
| | Adenine | 0.016 W/V % |
| | Glucose (anhydrous) | 0.801 W/V % |
| | Mannitol | 1.619 W/V % |
| | Citric acid | 0.022 W/V % |
| | Sodium citrate | 0.167 W/V % |
| | Monnosodium phosphate | 0.104 W/V % |

The adequate amounts of these erythrocyte preserving liquids to be used are about 18 to 22 in the case of the S.A.G.M liquid, about 22 ml in the case of the OPTISOL liquid, about 22 ml in the case of the ADSOL liquid, and about 22.5 ml in the case of the MAP liquid, based on the amount of erythrocyte separated from 100 ml of the whole human blood.

Figure 7:
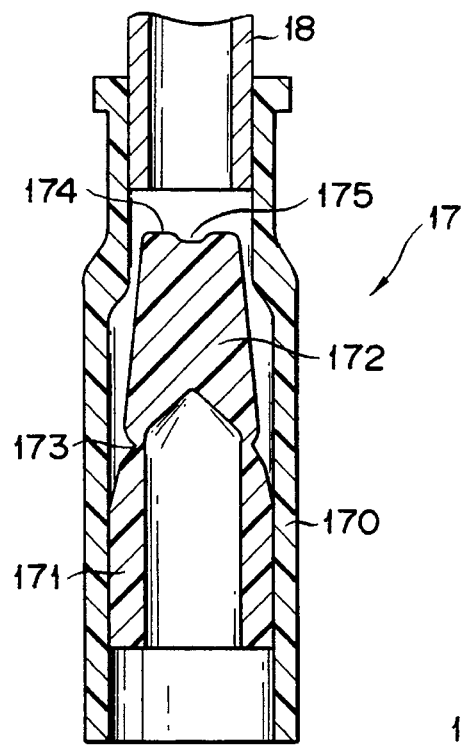
FIG. 7 is a longitudinal cross section illustrating on a magnified scale a connecting member to be used in this invention.

Now, the construction of the connecting member 17 will be described below. FIG. 7 is a longitudinal cross section illustrating one embodiment of the construction of the connecting member 17 on a magnified scale. As shown in the diagram, the connecting member 17 is composed of a short tube 170 formed of such a flexible resin as flexible polyvinyl chloride, for example, and a tubular member 171 watertightly inserted in the short tube 170 and having one end thereof blocked with a solid columnar part 172. The tubular member 171 functions as a blocking member which obstructs communication between the bag body 11 and the tube 18 and, on being fractured at a fracturing part 173 which will be described specifically hereinbelow, permits the communication mentioned above.

The tube 18 is watertightly connected at one end thereof to the upper end part in the bearings of FIG. 7 of the short tube 170. The lower end part in the bearings of FIG. 7 of the short tube 170 is watertightly attached or fused to the seal part 12 on the bag body 11.

The fracturing part 173 which is thin and brittle is formed on the periphery of the tubular member 171. The flow path is opened by the operator folding the solid columnar part 172 over itself together with the short tube 170 with the force of the operator's fingers exerted on the short tube 170 from outside thereby breaking the fracturing part 173 and inducing separation of the solid columnar part 172.

The materials which are effectively usable for the formation of the tubular member 171 include such hard materials as hard polyvinyl chloride, polycarbonate, and polyester, for example.

The upper part in the bearings of the diagram of the solid columnar part 172 has the shape of a wedge. An upper end part (apex) 174 thereof is preferable to be adapted so that the side thereof in the direction of width is smaller than the outside diameter of the tubular member 171 and larger than the inside diameter of the tube 18 and, therefore, the solid columnar part 172, on being fractured and separated, avoids blocking the tube 18. Optionally, the solid columnar part 172 may be provided in the upper end part 174 thereof with a groove 175 capable of promoting the flow of liquid.

The connecting member 24 and connecting members 27, 57, 61, 77, 79, and 81 which will be specifically described hereinbelow may be formed in the same construction as that which is shown in FIG. 7.

Figure 4:
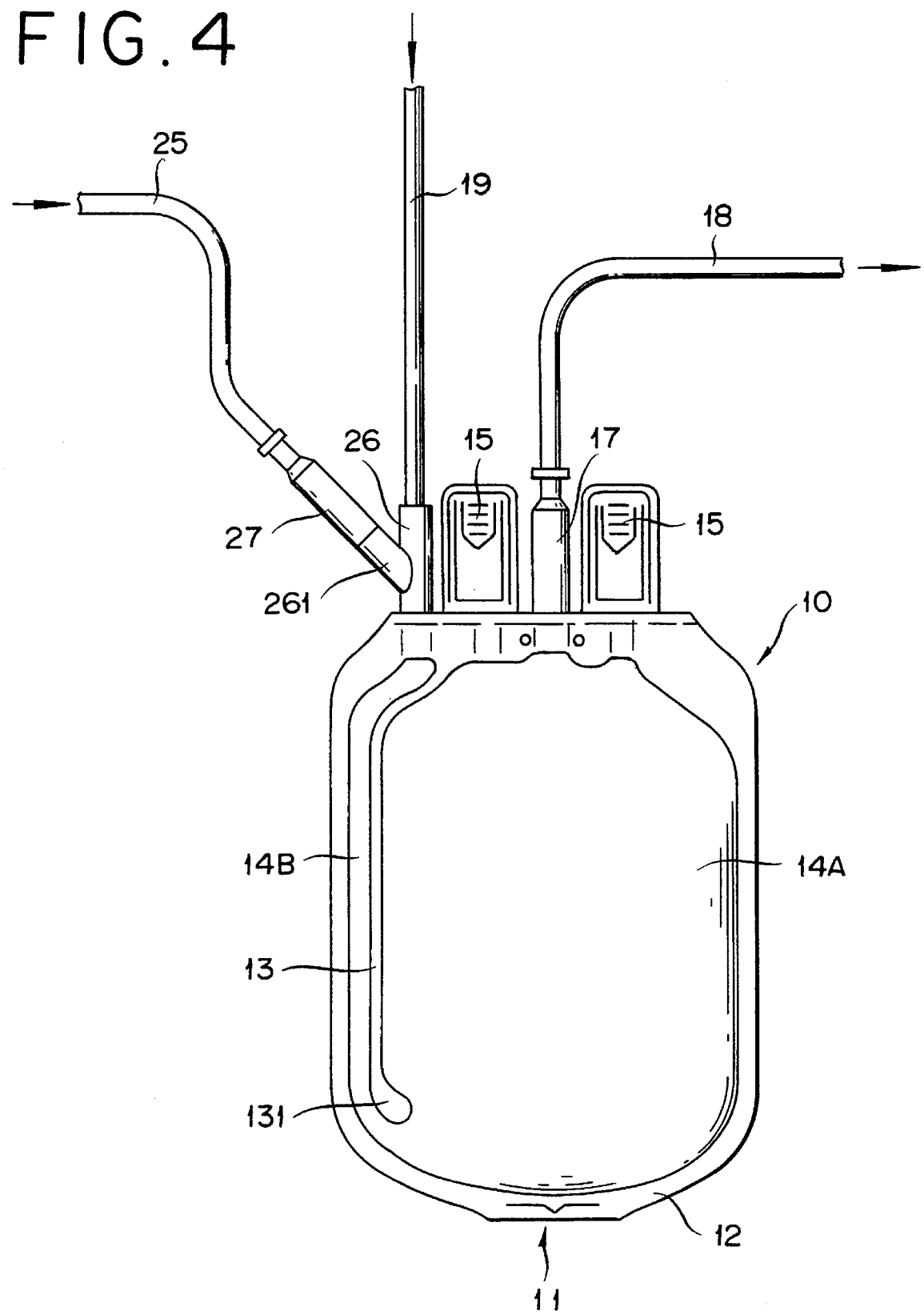
FIG. 4 is a plan view illustrating a further embodiment of the construction of the blood bag (blood collecting bag) to be used in this invention.

The blood collecting bag to be used in the present invention may be so constructed that the tube 19 for the introduction of blood communicates with the empty space 14B of the shape of a strip as shown in FIG. 4. In the blood collecting bag 10 shown in the diagram, the tube 19 is connected at one end thereof to the upper part of the bag body 11 through the medium of a branched connector 26 shaped like the letter Y so as to establish communication between the tube 19 and the empty space 14B.

The tube 25 communicating with the interior of the preserving liquid bag is connected at one end thereof to a branched tube 261 of the branched connector 26 through the medium of a connecting member 27 capable of opening a flow path thereof when the connecting member 27 is fractured in the same manner as described above. As a result, the empty space 14B of the blood collecting bag 10 and the interior of the preserving liquid bag are allowed to communicate with each other via the tube 25 when the flow path of the connecting member 27 is opened.

Further, in the blood collecting bag 10 illustrated in FIG. 4, the discharge ports 15 for transfusion which are each sealed openably with a peel tab in the same manner as described above are formed on the opposite sides of the connecting member 17.

Incidentally, in the blood collecting bag 10 illustrated in FIG. 4, the tubes 19 and 25 are interjoined through the medium of the branched connector 26 and then made to communicate with the empty space 14B. This arrangement is not always necessary. Optionally, the tubes 19 and 25 may be so constructed as to communicate severally with the empty space 14B at separate positions.

Figure 5:
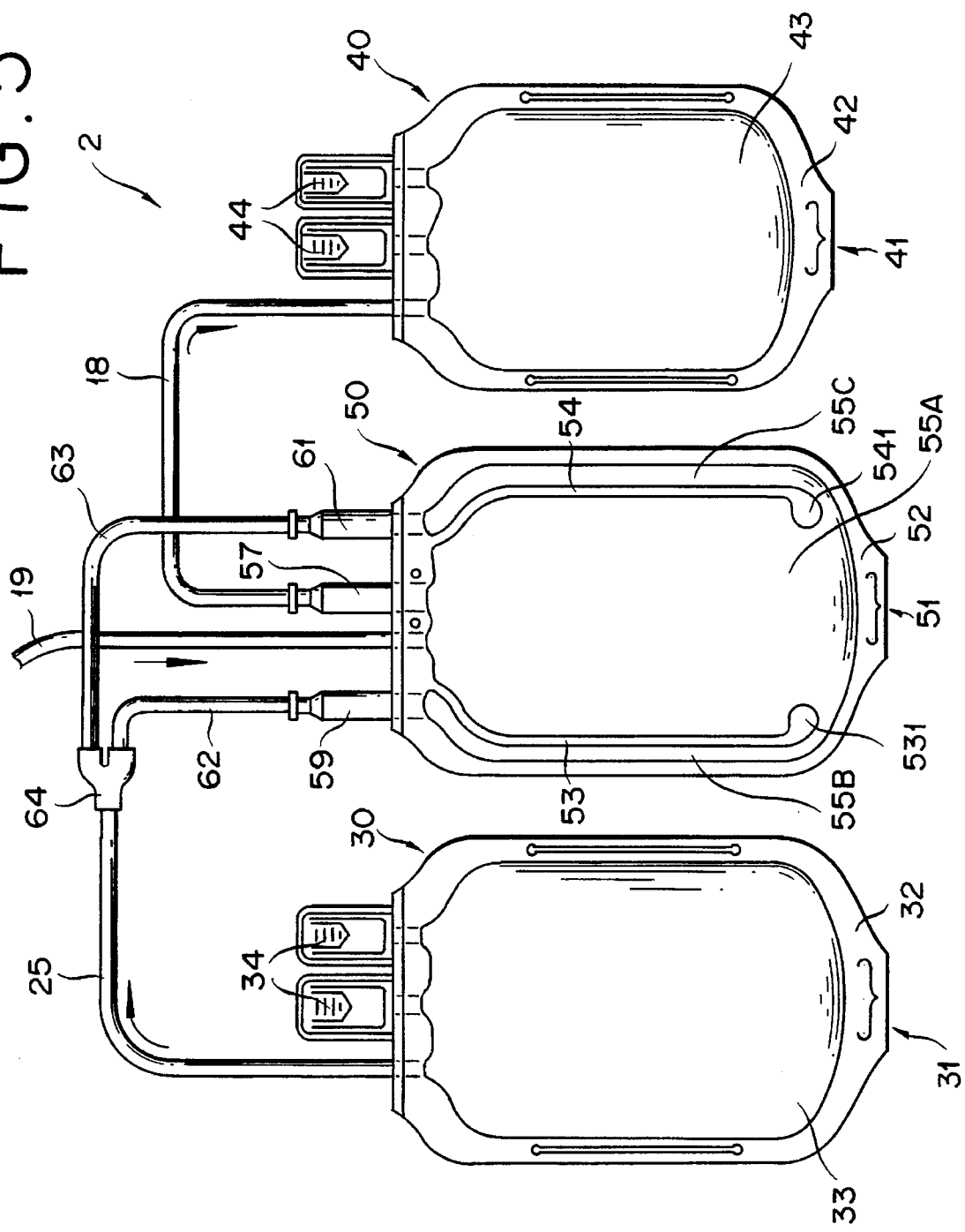
FIG. 5 is a plan view illustrating still another embodiment of the construction of the blood bag to be used in this invention.

The blood collecting bag to be used in the present invention may be constructed so that empty spaces 55B and 55C each of the shape of a strip are formed one each in the opposite lateral parts of the bag body as illustrated in FIG. 5 and the erythrocyte preserving liquid flows upwardly in the opposite sides of the bag body from below. A blood collecting bag 50 illustrated in FIG. 5 is adapted to give rise to a composite 2 of interconnected bags by being connected to the preserving liquid bag 30 and the blood plasma bag 40 which are constructed similarly to those in the aforementioned composite 1 of interconnected bags.

The blood collecting bag 50 comprises a bag body 51 which is constructed in a pouchy shape by superposing matched pieces of the same sheet material as mentioned above and fusing (by thermal fusion or high-frequency fusion, for example) or adhesively joining seal parts 52 of the superposed pieces along the periphery thereof.

The interior of the bag body 51 is divided by two partition strips 53 and 54 into three empty spaces, namely an empty space 55A which occupies the major part of the inner empty space of the bag body 51 and the empty spaces 55B and 55C formed each in the shape of a strip along the opposite lateral parts of the bag body 51. These empty spaces 55A, 55B, and 55C communicate with one another near end parts 531 and 541 respectively of the partition strips 53 and 54.

The upper ends of the partition strips 53 and 54 are connected to the seal part 52. The bag body 51 is preferable to be formed by melting or adhesively joining matched pieces of a sheet material in the same manner as described above. The widths of the partition strips 53 and 54 and the volumetric proportions, shapes, and dimensions (widths) of the empty spaces 55B and 55C are preferable to be severally selected in the ranges between the value which were specified above as desirable magnitudes for the empty space 14B and the values which are halves respectively of those values mentioned above.

Further, the shapes and radiuses of curvature of the end parts 531 and 541 of the two partition strips 53 and 54 are similar to those of the end parts 131 mentioned above. In this case, the end parts 531 and 541 may assume any of the positions corresponding to those indicated by W to Z in FIG. 2. The position of the end part 531 and that (height) of the end part 541 may be identical or different.

In the illustrated embodiment, the empty spaces 55B and 55C are formed symmetrically right to left in the bearings of the diagram. Optionally, the shapes and positions of these two empty spaces may be asymmetrical right to left.

On the bag body 51, a connecting member 57 is disposed so as to communicate with the empty space 55A. At the same time, the tube 19 for blood transfusion is connected at one end thereof to the upper part of the bag body 51. The tube 18 which has flexibility is connected at one end thereof to the connecting member 57. The tube 18 is connected at the other end thereof to the upper part of the blood plasma bag 40 and therefore enabled to communicate with the blood plasma storing part 43. As the result of this arrangement, the empty space 55A of the blood collecting bag 50 and the blood plasma storing part 43 of the blood plasma bag 40 are allowed to communicate with each other through the medium of the tube 18 when the flow path of the connecting member 57 is opened.

Connecting members 59 and 61 communicating respectively with the empty spaces 55B and 55C are provided in the opposite upper lateral parts of the bag body 51. Tubes 62 and 63 which have flexibility are connected at one end thereof respectively to the connecting members 59 and 61. The other ends of the tubes 62 and 63 are joined through the medium of a branched connector 64 shaped like the letter Y to one end of the tube 25. The tube 25 is connected at the other end to the upper part of the preserving liquid bag 30 and then made to communicate with the preserving liquid storing part 33. As the result of this arrangement, the empty spaces 55B and 55C of the blood collecting bag 50 and the preserving liquid storing part 33 of the preserving liquid bag 30 are allowed to communicate with one another through the medium of the tubes 62, 63, and 25 when the flow paths of the connecting members 59 and 61 are opened.

In the blood collecting bag 50 constructed as described above, the erythrocyte preserving liquid and the whole erythrocyte are evenly admixed and ideally blended because the erythrocyte preserving liquid separates into two streams and as such flows into the empty spaces 55B and 55C.

Figure 6:
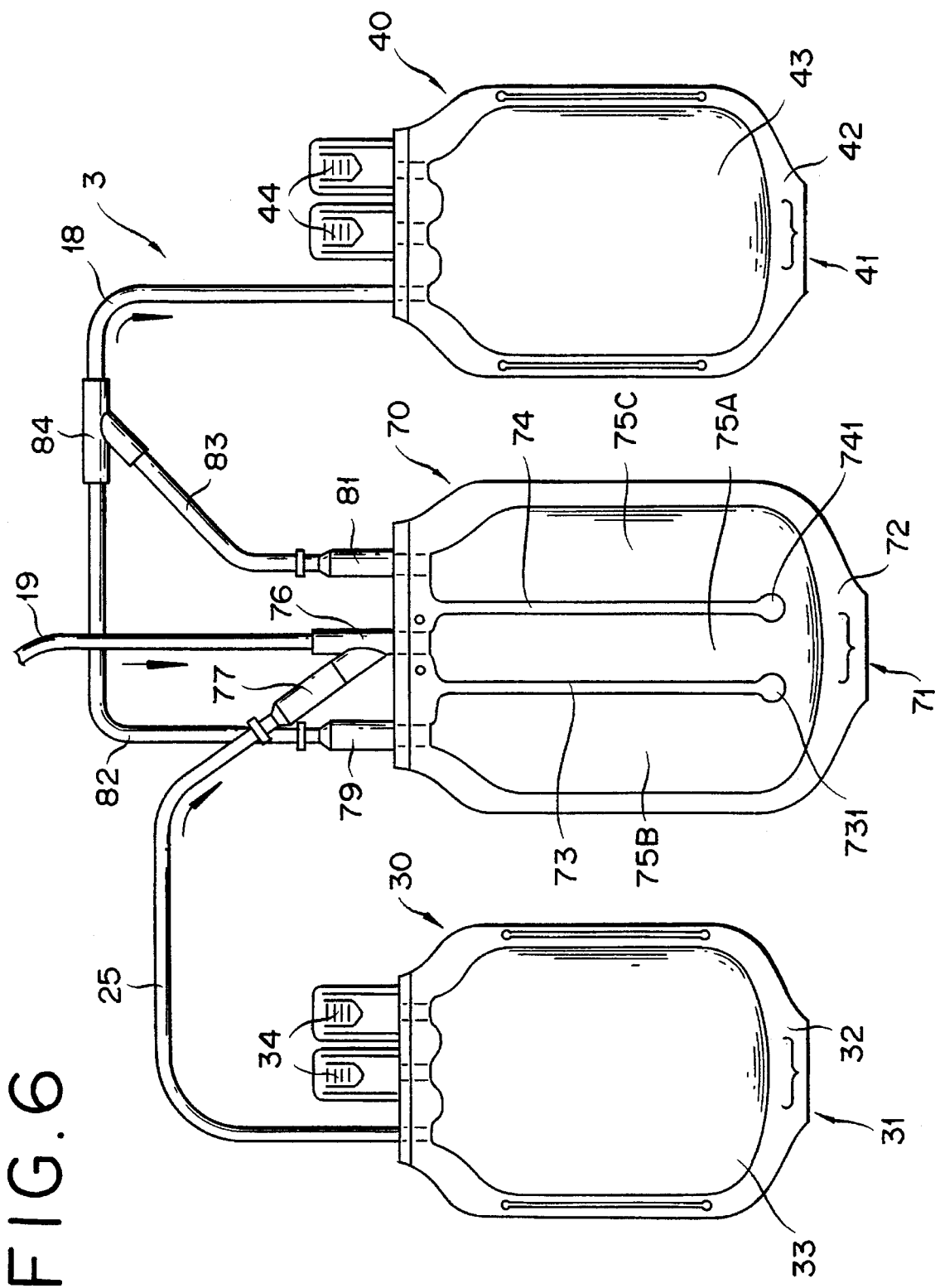
FIG. 6 is a plan view illustrating yet another embodiment of the construction of the blood bag to be used in this invention.

Further, the blood collecting bag to be used in the present invention may be constructed as illustrated in FIG. 6. A blood collecting bag 70 shown in FIG. 6 gives rise to a composite 3 of interconnected bags by being connected to the preserving liquid bag 30 and the blood plasma bag 40 which are constructed similarly to those of the composite 1 of interconnected bags described above.

The blood collecting bag 70 comprises a bag body 71 formed in a pouchy shape by superposing matched pieces of the same sheet material as described above and melting (by thermal melting or high-frequency melting, for example) or adhesively joining seal parts 72 of the superposed pieces along the periphery thereof.

The interior of this bag body 71 is divided by two partition strips 73 and 74 formed each in the shape of a strip along the opposite lateral parts of the bag body 71 into three empty spaces, namely an empty space 75A in the form of a strip and two empty spaces 75B and 75C positioned on the opposite sides of the empty space 75A. These empty spaces 75A, 75B, and 75C communicate with one another near the end parts 731 and 741 of the partition strips 73 and 74.

The partition strips 73 and 74 are connected at the upper ends thereof to the seal part 72. These partition strips 73 and 74 are preferable to be formed in the same manner as described above, i.e. by melting matched pieces of the same sheet material as used for the bag body 71.

The widths of the partition strips 73 and 74 and the shapes and radiuses of curvature of the end parts 731 and 741 of the two partition strips are the same as those of the end parts described above. In this case, the end parts 731 and 741 may assume positions corresponding to those indicated by W to Z in FIG. 2. The positions (heights) of the end part 731 and the end part 741 may be identical to or different from each other.

Further, such factors as the volumetric proportion, shape, and dimensions (width) of the empty space 75A are the same as those of the empty spaces 14B, 55B, and 55C described above.

A branched connector 76 shaped like the letter Y is connected to the upper part of the bag body 71 so as to communicate with the empty space 75A. The tube 19 for blood transfusion is connected at one end thereof to one of the shanks of the branched connector 76. The tube 25 communicating with the interior of the preserving liquid bag 30 is connected at one end thereof to the other shanks of the branched connector 76 through the medium of a similar connecting member 77. As the result of this arrangement, the empty space 55A of the blood collecting bag 50 and the preserving liquid storing part 33 of the preserving liquid bag 30 are allowed to communicate with each other through the medium of the tube 25 when the flow path of the connecting member 77 is opened.

Connecting members 79 and 81 communicating respectively with the empty spaces 55B and 55C are provided one each on the opposite upper lateral sides of the bag body 71. Tubes 82 and 83 which have flexibility are connected each at one end thereof to the connecting members 79 and 81. The tubes 82 and 83 are connected each at the other end thereof to one end of the tube 18 through the medium of a branched connector 84 shaped like the letter Y. The tube 18 is connected at the other end thereof to the upper part of the blood plasma bag 40 and consequently allowed to communicate with the blood plasma storing part 43. As the result of this arrangement, the empty spaces 75B and 75C of the blood collecting bag 50 and the blood plasma storing part 43 of the blood plasma bag 40 are allowed to communicate with one another through the medium of the tubes 82 and 83 when the flow paths of the connecting members 79 and 81 are opened.

Owing to the construction described above, the erythrocyte preserving liquid in the preserving liquid bag 30 flows into the empty space 55A via the tube 18, separates into two streams and as such joins the portions of concentrated erythrocyte which have been separated by an operation to be described specifically hereinbelow and placed in the empty spaces 75B and 75C.

The blood collecting bags 10, 50, and 70, the erythrocyte bag 30, and the blood plasma bag 40 are each formed by superposing matched pieces of a flexible sheet material and melting the conforming edges of the superposed pieces. These bags 10, 20, 30, 40, 50, and 70 are not always required to be constructed in the manner described above. They may be formed in a pouchy shape, for example, by concentrically superposing equally long tubes of the same sheet material as described above and melting (by thermal melting or high-frequency melting, for example) or adhesively joining the opposite (open) ends of the superposed tubes.

Figure 8:
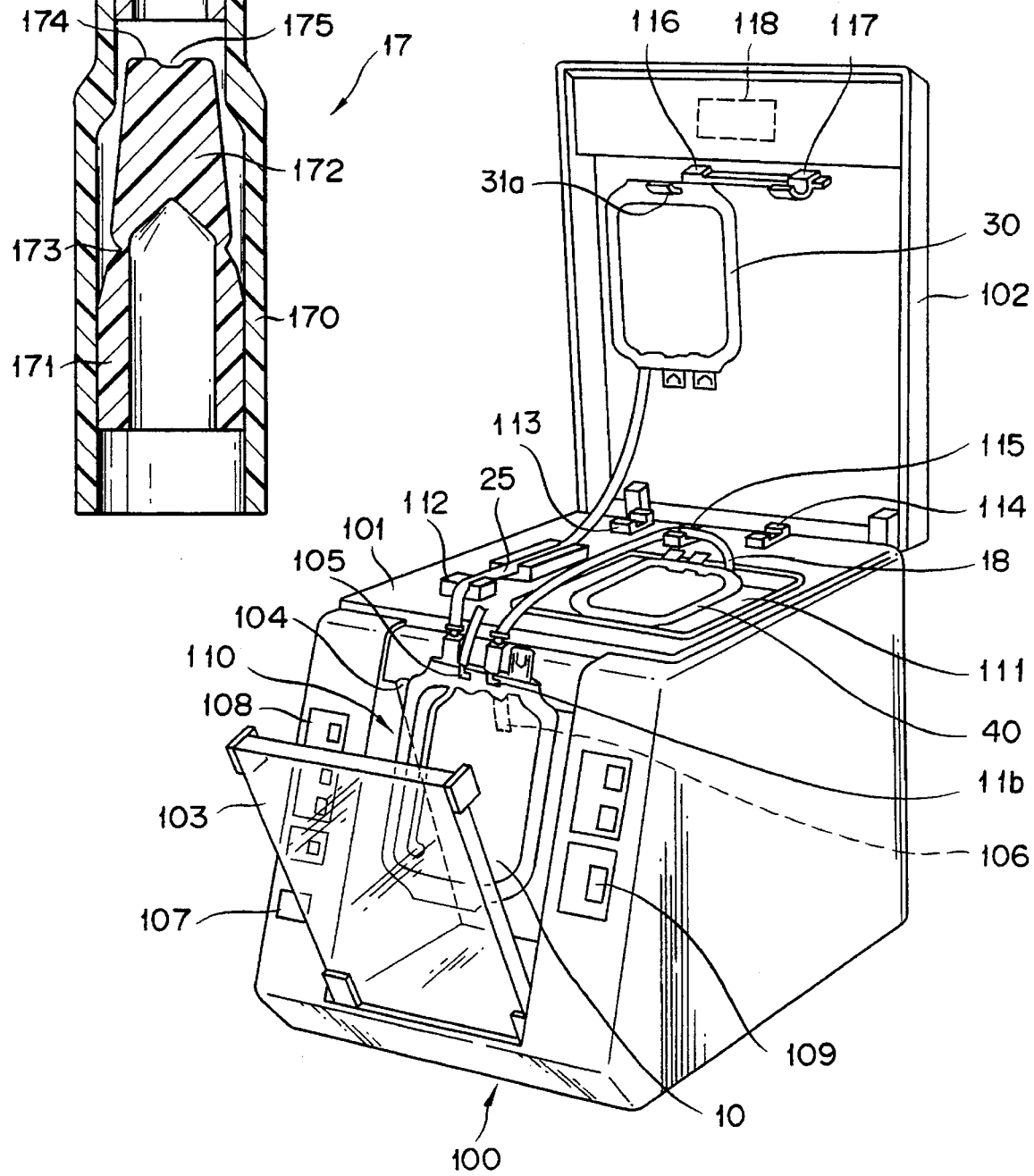
FIG. 8 is a perspective view illustrating one embodiment of an automatic blood analyzer having attached thereto the blood bag shown in FIG. 1.

FIG. 8 is a perspective view illustrating an automatic blood separating device having set in place therein the composite 1 of interconnected bags shown in FIG. 1 as one example of the means for centrifugally treating blood in the blood collecting bag 10 and then delivering the separated blood components to the relevant bags in accordance with the method of this invention for the treatment of blood.

An automatic blood separating device 100 is composed of a housing 101 and a lid 102. A first plate-like member 103 is attached swingably to the front surface of the housing 101 and a second plate-like member 104 is attached to the housing 101 as interposed between the housing 101 and the first plate-like member 102. A hook 105 adapted to pierce the hole 11b of the blood collecting bag 10 and retain the blood collecting bag 10 is disposed slightly above the second plate-like member 104. The second plate-like member 104 is provided with a sensing part 106. This sensing part 106 is intended to detect the boundary between the separated layers of blood components in the blood collecting bag 10. A photosensor, for example, is used as the sensing part 106 and is adapted to detect the boundary by virtue of the differences of the blood components in absorptance of light or transmittance of light and reflectance of light. On the front surface of the housing 101, a power source switch 107 and operating panels 108 and 109 fitted with various operating switches are disposed.

A blood collecting bag storing part 110 is formed with an interval between the first plate-like member 103 and the second plate-like member 104. The first plate-like member 103 is depicted in an opened state in FIG. 8. This first plate-like member 103 in the opened state is pushed into a closed state after the hook 105 is passed through the hole 11b and the blood collecting bag 10 is placed in the storing part 110. Inside the housing 101 is disposed means (not shown) for pressing the second plate-like member 104, which is adapted to diminish gradually the force of pressure generated after the liquid in the upper layer of the blood collecting bag 10 has verged on flowing out and then depress the second plate-like member 104.

On the upper surface of the housing, a storing part 111 (overlain by the blood plasma bag 40 as depicted in the diagram) and a first clamp 112, a second clamp 113, a third clamp 114, and a fourth clamp 115 for opening and closing the relevant tubes are disposed. These clamps are opened and closed with solenoids (not shown) attached respectively thereto. As illustrated in FIG. 8, the tube 25 is attached to the first clamp 112 and the tube 18 to the fourth clamp 115 respectively. The tray which forms the storing part 111 is provided with a weight sensor (not shown) which serves to sense the weight of the bag placed in the storing part 111.

The lid 102 is provided with hooks 116 and 117 which serve the purpose of suspending the individual bags which are connected to the blood collecting bag 10. As illustrated in FIG. 8, the preserving liquid bag 30 is suspended from the hood 116 by means of a slit 31a. The hooks 116 and 117 are supported by one single weight sensor 118 which is provided inside the lid 102.

The weight sensor 118, on discriminating between the opened state and the closed state of the clamps 113 and 114 when the bags are suspended by both the hooks 116 and 117, confirms that the outcome of the detection by the weight sensor 118 conforms to the change in weight of the bag connected to the tube which is attached to the side of the opened state and effects selective detection of the weights of the bags suspended from the hooks 116 and 117.

Then, the position of the boundary mentioned above detected automatically by the sensor 106 and the weights detected by the weight sensor of the storing part 111 and the weight sensor 118 can be set by the operation of the operating panels 108 and 109, depending on the inner volume of the blood collecting bag 10, the conditions for the centrifugal separation, etc. Then in accordance with the results of detection obtained by the sensing part 106 and the weight sensor (not shown) of the storing part 111 and the weight sensor 118, the operations of the depressing means of the plate-like member 104 and the first through fourth clamps 112, 113, 114, and 115 are automatically switched.

Now one example of the operation of separating blood components by the use of the automatic blood separating device explained above will be described below.

After the bags and tubes have been set in place as shown in the diagram and the position detected by the sensor 106 and the weight detected by the weight sensor 116 have been set by the operating panels 108 and 109, the first plate-like member 103 is closed, the connecting member 17 of the blood collecting bag 10 is fractured to open the flow path, and the switches for starting centrifugal separation provided on the operating panels 108 and 109 are depressed. As a result, the clamp 112 is set into a closed state and the clamp 115 into an opened state. Then, the pushing means mentioned above is set operating, the second plate-like member 104 is pushed toward the first plate-like member 103, and the blood plasma of the upper layer in the blood collecting bag 10 is caused to advance through the connecting means 17 and the tube 18 and flow into the blood plasma bag 40 placed in the storing part 111. The sensing part 106, on detecting the boundary between the layer of blood plasma and the layer of concentrated erythrocyte, sets the clamp 112 in an opened state and the clamp 115 in a closed state. At the same time, the second plate-like member 104 is relieved of the pressure and the first plate-like member 103 is released. At this time, the amount of blood plasma collected consequently is detected by the weight sensor of the storing part 111 and committed to storage in a memory (not shown) which is built in the device 100.

In the ensuant state of the device, the connecting member 24 of the blood collecting bag 10 is fractured to open the flow path. As a result, the head between the blood collecting bag 10 and the preserving liquid bag 30 induces the erythrocyte preserving liquid in the preserving liquid bag 30 to flow through the tube 25 and the connecting means 24 into the blood collecting bag 10. When the weight sensor 118 has discerned the fact the weight of the preserving liquid bag 30 has reached the prescribed level, namely that the prescribed amount of erythrocyte preserving liquid has flowed into the blood collecting bag 10, it sets the clamp 112 in a closed state and terminates the addition of the erythrocyte preserving liquid to the blood collecting bag 10.

In the separation of the blood into blood components by the use of the device described above, this invention allows for various alterations. It is permissible, for example, to have the tube 18 attached to the clamp 113, 114, or 115 instead of the clamp 112. Optionally, the operation of the pushing means mentioned above may be omitted by causing the weight sensor of the storing part 111 to discern the fact that the weight of the blood plasma bag 40 has reached the prescribed level.

The addition of the erythrocyte preserving liquid to the blood collecting bag 10 may be accomplished by having the erythrocyte preserving liquid placed in advance in a suitable amount in the preserving liquid bag 30 and allowing the whole amount of the preserving liquid to flow into the blood collecting bag 10 instead of using the sensor 118 and the clamp 113.

Further, for the separation of blood components into the relevant bags in accordance with this invention, the use of such an automatic blood separating device as illustrated in the diagram forms no essential requirement. A manual separation stand (not shown) may be used instead. This manual separation stand may be composed simply of a pair of pressing plates and a lever fixed on one of the pressing plate and operated by setting the blood collecting bag 10 between the two pressing plates, handling the lever thereby rotating one of the pressing plates about one side thereof as an axis of rotation and pressing this plate against the other pressing plate, and causing the blood collecting bag 10 to be squeezed between the two pressing plates.

For the purpose of disposing the preserving liquid bag 30 at a level higher than that of the blood collecting bag 10, a stand furnished with the equivalents of the hooks 116 and 117 mentioned above is prepared separately and used for suspending the preserving liquid bag 30 with the aid of the hooks.

Now, one method for the treatment of blood as a first embodiment of this invention will be described below with respect to a case of using the composite 1 of interconnected bags shown in FIG. 1 and the automatic blood separating device 100 shown in FIG. 8.

(1) The blood collecting needle 21 is thrust into the blood vessel and the blood consequently collected is introduced via the tube 19 into the blood collecting bag 10. At this time, the blood is guided through the tube 19 into the empty space 14A of the blood collecting bag 10 and the empty space 14A part of the bag body 11 is gradually inflated. In consequence of this inflation, the bag body 11 is deformed as though it were folded along the partition strip 13. As a result, the connecting part 141 between the two empty spaces 14A and 14B is kept in a closed state and virtually no blood enters the interior of the empty space 14B. Even if the blood happens to find its way into the empty space 14A, the empty space 14B during the course of the centrifugal separation which will be described more specifically hereinbelow is crushed between the inner wall surfaces of the centrifugal cap by virtue of the centrifugal force. Thus, the blood which remains in the empty space 14B is only in a small amount and the greater part of the remaining blood consists of erythrocyte. Particularly, the fact that the end part 131 of the partition strip 12 is so shaped as to possess the land part mentioned above benefits the closure of the connecting part 141.

The closure of the connecting part 141 may be ensured by having the portions of the superposed pieces of sheet material approximating the connecting part 141 blocked (by adhesion) in advance or effecting the closure by means of clamps, for example.

(2) After the introduction of the collected blood into the blood collecting bag 10 has been completed, the tube 19 is sealed as by means of fusion and the blood collecting needle 21 side part of the tube is removed by cutting from the sealing part.

(3) Then, a pile of the blood collecting bag 10, the preserving liquid bag 30, and the blood plasma bag 40 is placed in the centrifugal cup of the centrifugal separation device, with the bag body held in a posture such that the end part of the bag body 1 used for attachment thereto of the tubes 18 and 19 falls on the upper side (with the bottoms of the component bags lying on the lower side), and the pile is subjected to a centrifugal treatment. In the blood collecting bag 10, the tubes 18 and 19 are connected to one end part of the bag body 11 (the upper part of the blood collecting bag 10 in the bearings of the diagram). When the blood collecting bag 10 in the accessorized state is placed in the centrifugal cup, therefore, the tubes posed on the upper side offer no obstruction and the insertion of the blood collecting bag 10, etc. can be effected favorably. Further, the possibility that the bag will sustain damage because the otherwise possible protrusion of the tubes toward the bottom part of the bag gives rise to a dead space inside the centrifugal cup is precluded.

As a typical example of the centrifugal separator which is effectively usable herein, the product of Hitachi Koki Co., Ltd. marketed under product code of "CR-7B3" may be cited. In this case, the conditions of centrifugation generally adopted are 1,700 to 6,000 G and 4 to 10 minutes, for example. Even during the course of the centrifugal treatment, no blood is suffered to leak into the empty space 14B.

In consequence of the centrifugal treatment performed as described above, the blood in the empty space 14A separates into two layers, i.e. an upper layer of blood plasma and a lower layer of concentrated erythrocyte (not shown).

When the centrifugal treatment is started, concentration of stress tends to occur near the end part 131 of the partition strip 13 because the internal pressure in the lower part of the bag body increases and the lower part of the bag body further inflates as a consequence. In the embodiment illustrated in FIG. 1, since the end part 131 is shaped and adapted as described above, the end part 131 entails neither exfoliation nor cracking and, as a result, the bag body is prevented from fracture.

(4) After the centrifugal treatment has been completed, the composite 1 of interconnected bags is gently extracted from the centrifugal cup, the blood collecting bag 10, the preserving liquid bag 30, and the blood plasma bag 40 are set in place in the automatic blood separating device 100 as illustrated in FIG. 8 and, at the same time, the internal flow path of the connecting member 17 is opened as described above.

(5) The automatic blood separating device 100 is operated to press the blood collecting bag 10 gradually. In consequence of this gradual exertion of pressure, the blood plasma forming the upper layer is discharged through the connecting member 17 in the opened state and transferred via the tube 28 to the blood plasma storing part 43 of the blood plasma bag 40. The pressure causes the bag body 11 to assume a uniformly inflated form and the liquid pressure consequently generated relieves the connecting part 141 of the closed state. Since the end part of the partition strip 13 is positioned below the boundary between the layer of blood plasma and the layer of concentrated erythrocyte (on the bottom part side of the bag body 11), however, the possibility of the blood plasma flowing into the empty space 14B through the connecting part 141 which has been relieved of the closed state is nil.

During the discharge and transfer of the blood plasma just mentioned, the flow volume (flow rate) of the blood plasma may be adjusted by blocking the stream of the blood plasma in the tube 18 by nipping the tube 18 at a point conveniently selected in the length thereof by means of finger tips or a clamp, for example.

After the whole amount of the blood plasma stored in the blood collecting bag 10 has been discharged and transferred, the lower layer of concentrated erythrocyte is left behind in the bag body 11 of the blood collecting bag. At this point, the automatic blood separating device 100 is operated to relieve the blood collecting bag 10 of the applied pressure and, at the same time, switch the clamps 112 and 115. When the internal flow path of the connecting member 24 is opened as described above, the head between the preserving liquid bag 30 and the blood collecting bag 10 causes the erythrocyte preserving liquid stored in the preserving liquid bag 30 to flow via the tube 25 and the connecting member 24 in the opened state into the blood collecting bag 10.

In the blood collecting bag 10, the separated mass of concentrated erythrocyte remains in the substantially whole amount thereof in the empty space 14A which occupies the grater part of the empty space in the blood collecting bag 10. The erythrocyte preserving liquid, after flowing into the empty space 14B of the blood collecting bag 10, flows through the connecting part 141 into the empty space 14A, and joins itself upwardly into the mass of concentrated erythrocyte stored previously therein. When the addition of the concentrated red blood corpuscle preserving liquid is carried out as described above, the erythrocyte preserving liquid is advanced through the connecting part 141 and added evenly along the bottom surface of the bag body 11 into the mass of concentrated erythrocyte helds inside the empty space 14A. Since the preserving liquid is caused by the force of the inflow thereof to mingle with the concentrated erythrocyte to a certain extent, the operation of this invention can be effectively manifested.

(6) After the erythrocyte preserving liquid stored in the preserving liquid bag 30 has been transferred in the prescribed amount into the blood collecting bag, the addition of the erythrocyte preserving liquid into the blood collecting bag 10 is terminated by switching the clamp 112 and closing the tube 18. The tubes 18 and 25 are sealed as by melting each at two points along the length thereof and the portions of the tubes 18 and 25 intervening between the melting points are severed from the respective remainders before the blood collecting bag 10, the preserving liquid bag 30, and the blood plasma bag 40 are separated from one another. As a result, the blood collecting bag 10 and the blood plasma bag 40 respectively containing the concentrated erythrocyte and the blood plasma in a tightly sealed state are obtained.

In the blood collecting bag which contains the concentrated erythrocyte with the erythrocyte preserving liquid added to the lower part thereof, therefore, the erythrocyte preserving liquid having a smaller specific gravity gradually ascends as diffusing in erythrocyte and the erythrocyte having a larger specific gravity gradually settles and the erythrocyte preserving liquid and the erythrocytes are thoroughly stirred by following the course of nature without requiring any special treatment.

Incidentally, the time required for the erythrocyte preserving liquid to mingle thoroughly with the concentrated erythrocyte falls in the approximate range of 15 minutes to one hour. The erythrocyte fresh form the separation can be safely used for transfusion even immediately after the elapse of this time.

(7) The extraction of the concentrated erythrocyte from the blood collecting bag 10 is attained after the peel tab of the discharge port 15 has been ripped open. The blood collecting bag 10 is then readied for transfusion by having a transfusion set joined thereto. By the same token, the fracture of the peel tab of the discharge port 44 is required to precede the extraction of the blood plasma from the blood plasma bag 40. The blood plasma bag 40 is readied for transfusion by having a transfusion set joined thereto.

The procedure described above can be wholly carried out with the blood collecting bag 10 kept in posture such that the side of the bag 10 to which the tubes 18 and 19 are connected falls on the upper side. The extra work otherwise required in turning the bag upside down, therefore, is obviated when the bag is to be readied for the addition thereto of the erythrocyte preserving liquid.

The embodiment given above has been depicted as adopting an arrangement such that the transfer of the erythrocyte preserving liquid into the blood collecting bag 10 is attained by virtue of the head between the preserving liquid bag 30 and the blood collecting bag 10. Alternatively, the transfer may be accomplished by the use of a means for applying pressure to the preserving liquid bag or a means such as a roller pump which advances a liquid through a conduit.

Now, the second embodiment of the method of this invention for the treatment of blood will be described in detail with reference to the accompanying drawings.

Figure 9:
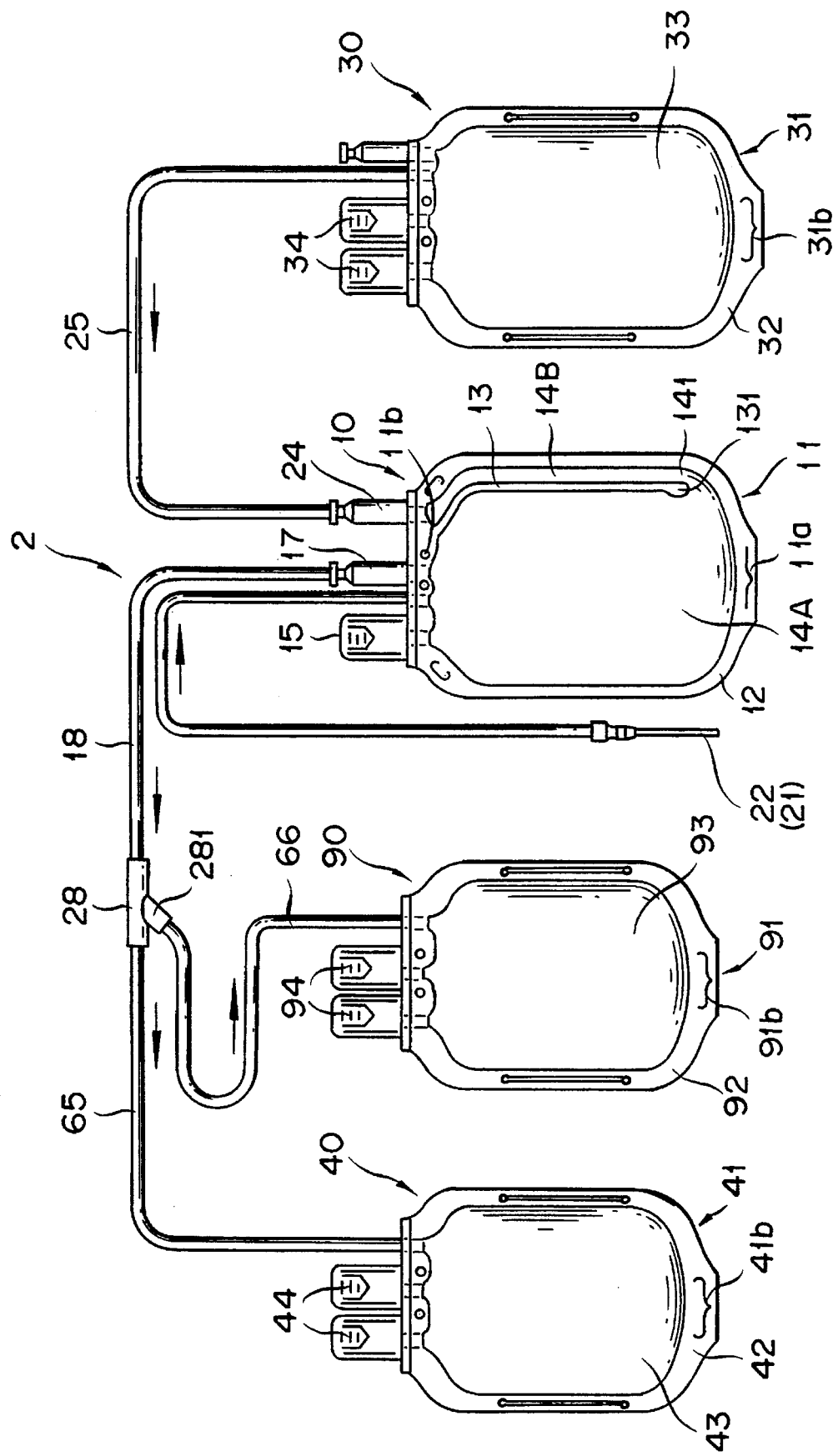
FIG. 9 is a plan view illustrating a further embodiment of the construction of the blood bag to be used in this invention.

FIG. 9 is a plan view illustrating an embodiment of the construction of a blood collecting bag to be used in the second embodiment of the method of this invention for the treatment of blood. In FIG. 9 and in FIGS. 1 through 7 already used in the description of this invention, like reference numerals refer to like or corresponding parts. These parts, therefore, will be omitted from the following detailed description.

A composite 4 of interconnected bags illustrated in FIG. 9 is adapted to separate blood into an upper layer of blood plasma, an intermediate layer of buffy coat (containing leukocyte and blood platelets), and a lower layer of concentrated erythrocyte. The composite 4 is provided with a buffy coat bag 90 for storing the buffy coat of the intermediate layer separately of the blood plasma. The construction of this composite 4 is substantially identical with that of the composite 1 of interconnected bags shown in FIG. 1, except for the inclusion of this buffy coat bag 90.

A branched connector 28 shaped like the letter Y is connected at one end thereof to one end of the tube 18 the other end of which is connected to the connecting member 17 which is provided on the bag body 11 of the blood collecting bag 10. A tube 66 is connected at one end thereof to a branched pipe 281 of the branched connector 28 and at another end thereof to the upper part of the buffy coat bag 90 which will be described specifically hereinbelow. A tube 65 is connected at one end thereof to the remaining end of the branched connector 28. The tube 65 is connected at the other end thereof to the upper part of the blood plasma bag 40. As a result of this arrangement, the interior of the blood plasma bag 40 and the interior of the buffy coat bag 90 are allowed to communicate with the empty space 14A of the blood collecting bag 10 through the medium of the tubes 18, 65, and 66 and the branched connector 28 when the connecting member 17 is opened.

The buffy coat bag 90 comprises a pouchy bag body 91 which is produced by superposing matched pieces of the same sheet material of flexible resin as used in the various bags mentioned above and melting (by thermal melting or high-frequency melting, for example) or adhesively joining seal parts 92 of the superposed pieces of the sheet material along the periphery thereof. In the inner part of the bag body 91 enclosed with the seal part 92, a buffy coat storing part 93 for storing the buffy coat separated from the blood in the blood collecting bag 1 is formed.

Further, on the buffy coat bag 90, two transfusion discharge ports 94 and 94 each sealed openably with a peel. tab are formed. In the bottom part of the seal part, a slit 91a similar to the slit 11a mentioned above is formed.

The thickness of the sheet material of which the buffy coat bag 90 is formed is decided in consideration of the strength required to withstand the impact of the centrifugal treatment and the softness. Generally, it is preferable to be in the approximate range of 0.2 to 0.7 mm, preferably 0.3 to 0.5 mm, though variable with the substance used for the sheet material.

Though the inner volume of the buffy coat bag 90 is not particularly restricted, it is in the approximate range of 80 to 200 ml, preferably 80 to 150 ml, in the case of the products prevailing in Japan or in the approximate range of 80 to 250 ml, preferably 80 to 200 ml, in the case of the products prevailing in foreign countries.

Figure 10:
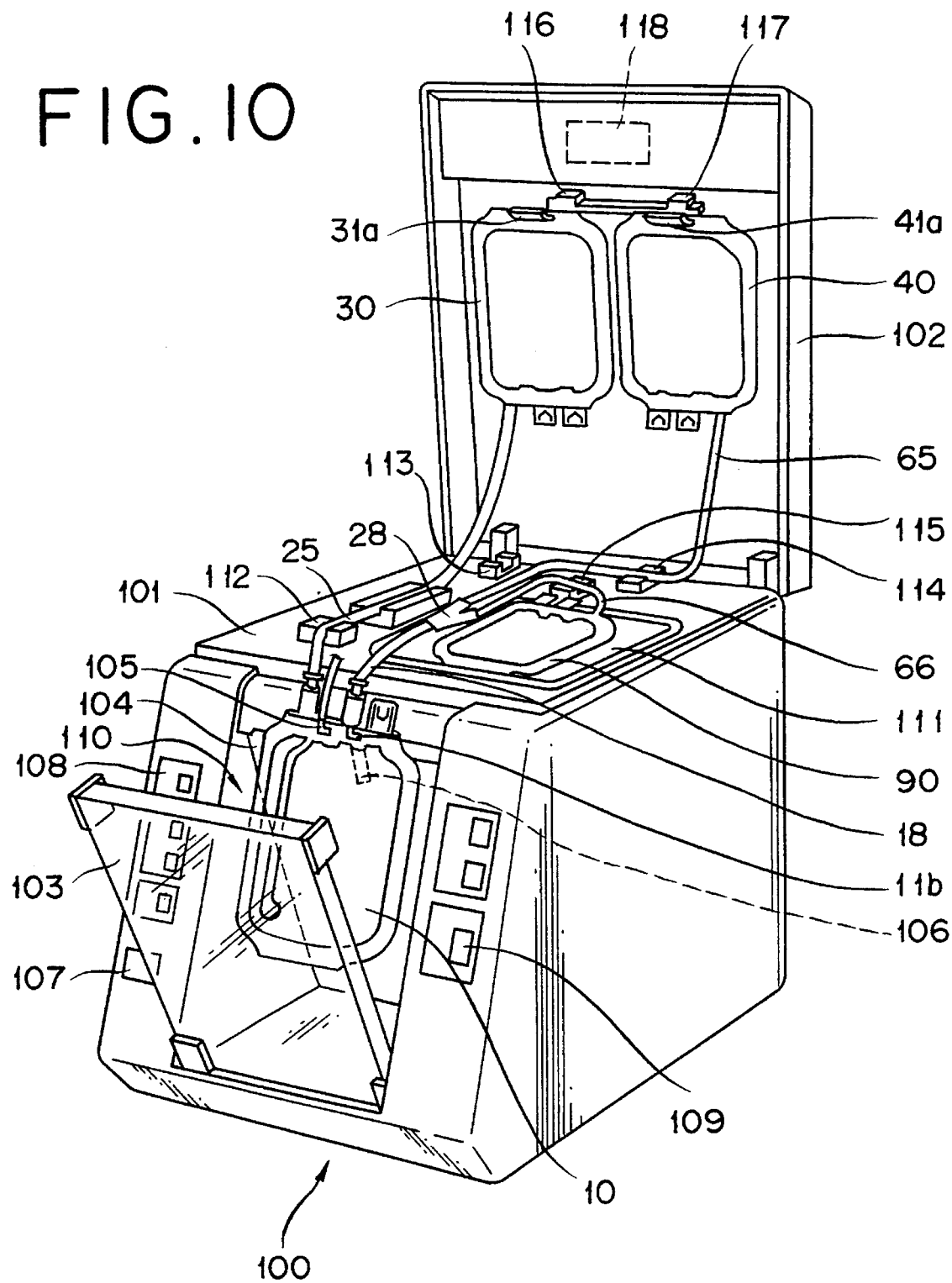
FIG. 10 is a perspective view illustrating one embodiment of an automatic blood analyzer having attached thereto the blood bag shown in FIG. 9.

FIG. 10 is a perspective view illustrating an automatic blood separating device having set therein the composite 4 of interconnected bags as one embodiment of the means used in the second embodiment of the method of this invention for the treatment of blood for the operation of centrifuging the blood in the blood collecting bag 10 and then distributing the separated blood components among the relevant bags. Now, the automatic blood separating device will be described below with reference to the diagram. The same matters as used in the embodiment illustrated in FIG. 8 will be omitted from the following description.

The automatic blood separating device 100 is identical in construction with that which is illustrated in FIG. 8. Similarly to the device of FIG. 8, the blood collecting bag 10 is encased in the storing part 110 and the preserving liquid bag 30 is suspended by the hook 116 with the aid of the slit 31a. In the device of FIG. 10, the buffy coat bag 90 is mounted on the storing part 111, the blood plasma bag 40 is suspended from the hook 117 which is not used in the device of FIG. 8 with the aid of the slit 41a, the tube 25 is attached to the first clamp 112 and the tube 65 to the third clamp 114, and the tube 66 is attached to the fourth clamp 115.

Now, one embodiment of the method for using the automatic blood separating device mentioned above will be described below.

First, the bags and the tubes are laid out as illustrated and the position to be sensed by the sensing part 106, the weight to be detected by the weight sensor of the storing part 111, and the weight to be detected by the weight sensor 118 are set. Then, the first plate-like member 103 is closed, the connecting member 17 of the blood collecting bag 10 is fractured as described above to open the internal flow path, and the switch for starting separation is depressed. As a result, the clamps 112 and 115 each assume a closed state and the clamp 114 assumes an opened state. Then, the pressure means mentioned above is set operating, the second plate-like member 104 is pressed toward the first plate-like member 103, and the blood plasma of the upper layer in the blood collecting bag 10 is caused to flow through the connecting means 17, the tube 18, the branched connector 28, and the tube 65 into the blood plasma bag 40 suspended from the hook 117.

The second plate-like member 104 ceases to be pressed, the clamp 115 assumes and open state, and the clamps 112 and 115 assume a closed state after the sensing part 106 has sensed the boundary between the layer of blood plasma and the layer of buffy coat. Thereafter, the pressure means of the second plate-like member 104 is again set operating the buffy coat in the blood collecting bag 10 is caused to flow through the connecting means 17, the tube 18, the branched connector 28, and the tube 66 into the buffy coat bag 90 mounted in the storing part 111.

The weight sensor which is provided in the storing part 111 discriminates whether or not the weight of the buffy coat bag 90 has reached the prescribed level. After the fact that the cumulative weight of the buffy coat introduced into the buffy coat bag 90 has reached the prescribed level is sensed as described above, the clamp 112 assumes and open state and the clamps 114 and 115 assume a closed state. At the same time, the second plate-like member 104 ceases to be pressed and the first plate-like member 103 is opened.

In the ensuant state of the device, the connecting member 24 of the blood collecting bag 10 is fractured to open the flow path thereof. As a result, the head between the blood collecting bag 10 and the preserving liquid bag 30 induces the erythrocyte preserving liquid in the preserving liquid bag to advance through the tube 25 and the connecting member 24 and flow into the blood collecting bag 10. Then, the weight sensor 118, on discerning the fact that the weight of the preserving liquid bag 30 has reached the prescribed level, i.e. the fact that the cumulative weight of the erythrocyte preserving liquid introduced in the blood collecting bag 10 has reached the mark, the clamp 112 assumes a closed state to terminate the addition of the red blood corpuscle preserving liquid into the blood collecting bag 10.

Now, the second embodiment of the method of this invention for the treatment of blood will be described below with respect to a case of adopting the composite 4 of interconnected bags shown in FIG. 9 and the automatic blood separating device 100 shown in FIG. 10.

(1) In the same manner as when the composite 1 of interconnected bags shown in FIG. 1 is adopted, the blood which has been collected by means of the blood collecting needle 21 is introduced into the blood collecting bag 10 via the tube 19 and the tube 19 is sealed as by melting and the blood collecting needle 21 side portion of the tube is severed by cutting from the sealed part.

(2) Then, the blood collecting bag 10, the preserving liquid bag 30, the blood plasma bag 40, and the buffy coat bag 90 are piled, the pile of these bags is placed in the centrifugal cup of the centrifugal separating device with the pile held in a posture such that the bottom parts of the bags fall on the lower side, and the bags of the pile are subjected to a centrifugal treatment. The same commercially available centrifugal separating device as mentioned previously can be used for the centrifugal treatment. In this case, the conditions of centrifugation are generally selected in the approximate ranges of 1,700 to 6,000 G and 4 to 10 minutes.

In consequence of the centrifugal treatment performed as described above, the blood in the empty space 14A is separated substantially into three layers, i.e. and upper layer of blood plasma, an intermediate layer of buffy coat, and a lower layer of concentrated erythrocyte (not shown).

(3) After the centrifugal treatment, the composite 4 of interconnected bags is gently extracted from the centrifugal cup, the composite 4 of interconnected bags is set in the automatic blood separating device 100 as illustrated in FIG. 10, and the internal flow path of the connecting member 17 is opened meanwhile as described above.

(4) The automatic blood separating device is operated so as to press the blood collecting bag 10 gradually. As a result, the blood plasma of the upper layer is discharged through the connecting member 17 in the opened state and transferred via the tubes 18 and 65 into the blood plasma storing part 43 of the blood plasma bag 40. At this time, the possibility of the blood plasma leaking into the tube 66 is nil because the tube 66 is in a closed state.

(5) After substantially the whole amount of the blood plasma in the blood collecting bag 10 has been discharged and transferred, the clamps 114 and 116 are switched to continue the application of pressure to the blood collecting bag 10. As a result, the buffy coat of the intermediate layer is advanced through the connecting member 17 in an opened state and transferred through the tubes 18 and 66 into the buffy coat storing part 93 of the buffy coat bag 90. At this time, the possibility of the buffy coat leading into the tube 65 is nil because the tube 65 is in a closed state.

(6) After substantially the whole amount of the buffy coat in the blood collecting bag 10 has been discharged and transferred, the concentrated erythrocyte of the lower layer are left behind in the bag body 11 of the blood collecting bag 10. At this time, the blood collecting bag 10 is relieved of the pressure and, at the same time, the first clamp 112 is set in an opened state and the internal flow path of the connecting member 24 is subsequently opened as described above. As a result, the head between the preserving liquid bag 30 and the blood collecting bag 10 induces the erythrocyte preserving liquid in the preserving liquid bag 30 to flow through the tube 25 and the connecting member 24 in an opened state into the blood collecting bag 10.

Incidentally, the opening of the flow path of the connecting member 24 may be carried out before the time mentioned above, e.g. at the same time that the flow path of the connecting member 17 is opened, so long as the first clamp 112 is kept in a closed state.

Inside the blood collecting bag 10, the erythrocyte preserving liquid first flows into the empty space 14B of the bag body 11 and further flows through the connecting member 141 into the empty space 24A and evenly joins itself along the bottom surface of the bag body 11 to the concentrated erythrocyte in the empty space 14A in much the same way as already described.

(7) After the cumulative amount of the erythrocyte preserving liquid transferred from the preserving liquid bag 30 into the blood collecting bag has reached the prescribed level, the clamp 112 is switched to close the tube 25 and terminate the addition of the erythrocyte preserving liquid to the blood collecting bag 10. The tubes 18 and 25 are sealed as by melting, for example, each at two points in the length thereof and the portions of the tubes 18, 25, and 29 which intervene between the sealed points are severed to set the blood collecting bag 10, the preserving liquid bag 30, the blood plasma bag 40, and the buffy coat bag 90 asunder. As a result, the blood collecting bag 10, the blood plasma bag 40, and the buffy coat bag 90 having the concentrated erythrocyte, the buffy coat, and the blood plasma respectively contained therein in a tightly sealed state are obtained.

Then, the erythrocyte preserving liquid and the erythrocyte are thoroughly stirred naturally without requiring any special treatment in much the same manner as already described because the erythrocyte preserving liquid having a smaller specific gravity gradually ascends as diffusing in the erythrocyte and the erythrocyte having a larger specific gravity gradually settle inside the blood collecting bag 10.

The method for the treatment of blood has been described thus far with respect to a case of adopting the composite of three or four interconnected bags. The method of this invention for the treatment of blood has no particular restriction except for the requirement that the blood components other than the concentrated erythrocyte should be discharged out of the blood collecting bag and thereafter the erythrocyte preserving liquid should be added upwardly to the concentrated erythrocyte from below.

The composite of interconnected bags to be used in the method of this invention for the treatment of blood does not need to be limited to the examples of construction cited above. The method may be used with a single-bag composite formed solely of a blood collecting bag, a double-bag composite formed of a blood collecting bag connected to either a blood plasma bag or an erythrocyte bag, a triple-bag composite formed of three bags any of which differs from the aforementioned bags in terms of use and content, and a composite formed of the component bags of the triple-bag composite mentioned above plus at least one bag selected from among such other bags as a blood platelet storing bag, a cryoprecipitate (AHF) recovering bag, and a leukocyte removing bag, for example.

Now, the present invention will be described specifically below with reference to working examples.

EXAMPLE 1

A composite of interconnected bags constructed as shown in FIG. 1 was produced by preparing a blood collecting bag, a preserving liquid bag, and a blood plasma bag satisfying the conditions shown below and interconnecting these bags with tubes (having an inside diameter, c, of 3 mm) made of flexible polyvinyl chloride. As the erythrocyte preserving liquid, 90 ml of the MAP liquid was sealed in the preserving liquid bag. Experiment 1 which is shown below was performed on the composite of interconnected bags, with the erythrocyte preserving liquid introduced via the empty space 14A and the connecting part 141 into the empty space 14B and added upwardly to the concentrated erythrocyte in the empty space 14B of the blood collecting bag from below.

(1) Sheet material for bag

The sheet materials of which the blood collecting bag, the preserving material bag, and the blood plasma bag were formed were invariably made of flexible polyvinyl chloride containing di(ethylhexyl) phthalate (DEHP) as a plasticizer in an amount in the range of 50 to 55 parts by weight, based on 100 parts by weight of the polyvinyl chloride. The sheet material had a thickness of 0.4 mm.

(2) Partition strip in blood collecting bag

The partition strip 13 was disposed as shown in FIG. 2, with the end part 131 of this partition strip 13 positioned at the middle point between X and Y in the diagram of FIG. 2.

The width of the partition strip (in the part thereof excluding the end part 131) H was 3 mm.

The end part (land Part) 131 of the partition strip 13 was shaped like a waterdrop as shown in FIG. 1. The radius of curvature R of the end part was about 3 mm (1.0 H).

(3) Empty spaces of blood collecting bag

The blood collecting bag 10 was manufactured so that the empty space 14B of the shape of a strip had a substantially fixed width the minimum magnitude a of which was 10 mm (a/f=0.15).

The inner volume of the empty space 14B of the blood collecting bag 10 was about 1.4% of the inner volume (456 ml) of the empty space 14A.

Control 1

Figure 11:
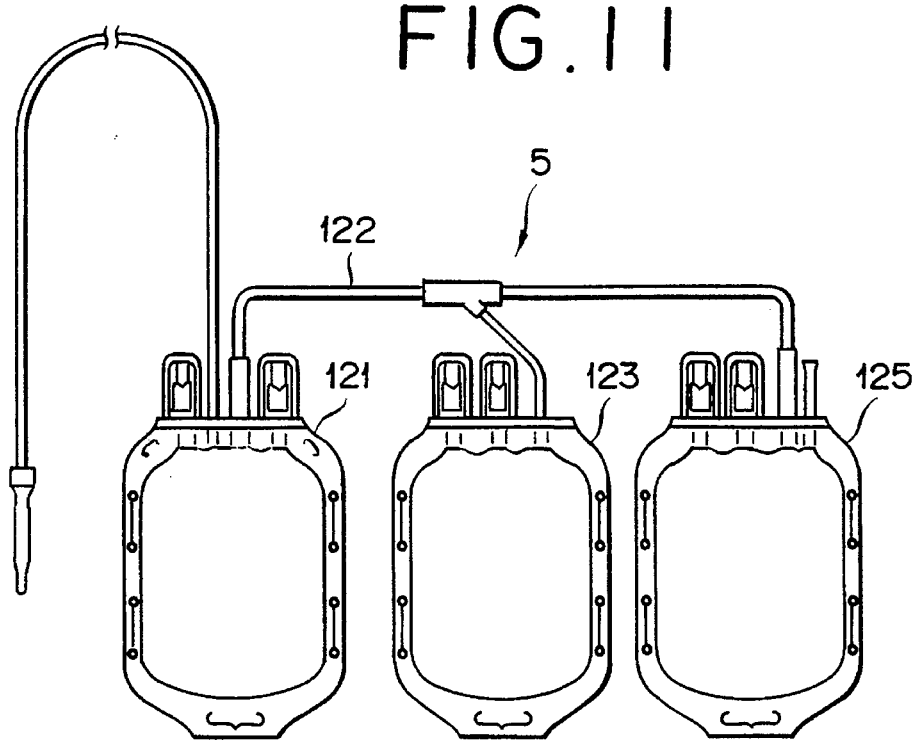
FIG. 11 is a plan view illustrating one embodiment of the conventional blood bag.

A composite of interconnected bags constructed as shown in FIG. 11 was manufactured by connecting a blood collecting bag devoid of a partition strip to a preserving liquid bag and a blood plasma bag with tubes (inside diameter c=3 mm) made of flexible polyvinyl chloride. Experiment 1 mentioned above was performed on the composite of interconnected bags, with the erythrocyte preserving liquid added upwardly to the concentrated erythrocyte in the blood collecting bag from below.

EXPERIMENT 1

A given composite of interconnected bags was subjected to sterilization with high-pressure steam. In the blood collecting bag, 56 ml of the CPD liquid (having the composition shown in Table 1) was placed as an anticoagulant agent. By means of a blood collecting needle, 400 ml of whole human blood was collected in the blood collecting bag. The composite containing the collected blood in the blood collecting bag was centrifuged with a centrifugal separating device (produced by Hitachi Koki Co., LtD. and marketed under product code of "CR-7B3") under the conditions of 3,300 G and 6 minutes.

Then, the component bags of the composite of interconnected bags were set in place as prescribed in an automatic blood separating device (product of Terumo K. K. and marketed under product code of "AC-211"). This automatic blood separating device was operated to effect centrifugation as prescribed. Of the blood components separated in two layers within the blood collecting bag, the platelet deficient blood plasma (PPP) of the upper layer was transferred to the blood plasma bag. Then, the erythrocyte preserving liquid in the preserving liquid bag was transferred to the blood collecting bag and added to the concentrated erythrocyte (CRC) left behind in the blood collecting bag.

The blood collecting bag which contained the concentrated erythrocyte incorporating therein the added erythrocyte preserving liquid was left standing in a refrigerator at 4° C. without stirring the erythrocyte. At the end of one week's standing in the refrigerator, the blood collecting bag was visually examined to determine whether or not the content thereof had formed floccules. The results are shown in Table 3.

EXAMPLE 2

A composite of interconnected bags constructed as shown in FIG. 9 was manufactured by connecting a blood collecting bag, a preserving liquid bag, a blood plasma bag, and a buffy coat bag satisfying the following conditions with tubes (inside diameter c=3 mm) made of flexible polyvinyl chloride.

(1) Sheet material for bag Same as in Example 1.

(2) Partition strip of blood collecting bag Same as in Example 1.

(3) Empty spaces of blood collecting bag Same as in Example 1.

Experiment 2 which is shown below was performed on the composite of interconnected bags, with the erythrocyte preserving liquid introduced via the empty space 14B and the connecting part 141 into the empty space 14B and added upwardly to the concentrated erythrocyte in the empty space 14B of the blood collecting bag from below.

CONTROL 2

Figure 12:
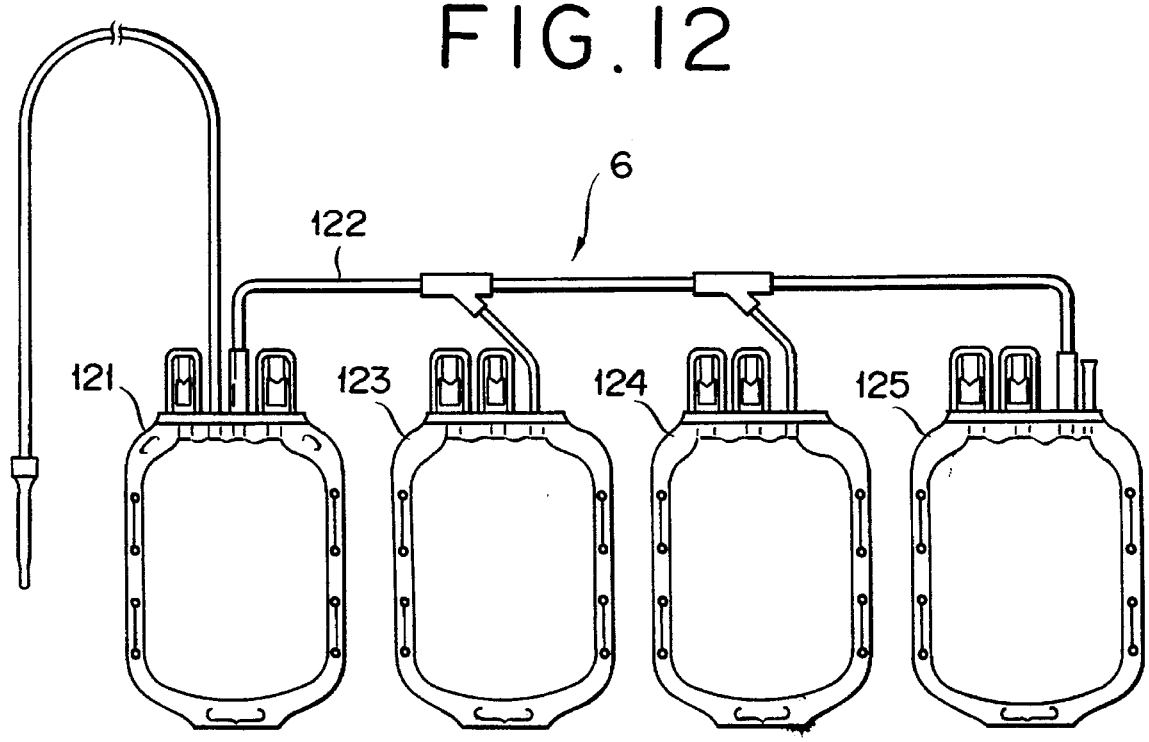
FIG. 12 is a plan view illustrating another embodiment of the conventional blood bag.

A composite of interconnected bags constructed as shown in FIG. 12 was manufactured by connecting a blood collecting bag devoid of a partition strip, a preserving liquid bag, a blood plasma bag, and a buffy coat bag with tubes (inside diameter c=3 mm) made of flexible polyvinyl chloride.

Experiment 2 mentioned above was performed on the composite of interconnected bags, with the erythrocyte preserving liquid added downwardly into the concentrated erythrocyte in the blood collecting bag form above.

EXPERIMENT 2

A given composite of interconnected bags was subjected to sterilization with high-pressure steam. Then, in the blood collecting bag, 56 ml of the CPD liquid (having the composition shown in Table 1) was placed as an anticoagulant agent. By means of a blood collecting needle, 400 ml of whole human blood was collected in the blood collecting bag. The composite containing the collected blood in the blood collecting bag was centrifuged with a centrifugal separating device (produced by Hitachi Koki Co., Ltd. and marketed under product code of "CR-7B3) under the conditions of 3,300 G and 6 minutes.

Then, the component bags of the composite of interconnected bags were set in place as prescribed in an automatic blood separating device (produced by Terumo K. K. and marketed under product code of "AC-211"). This automatic blood separating device was operated to effect prescribed separation. Of the blood components separated into three layers within the blood collecting bag, the platelet deficient blood plasma (PPPC) of the upper layer was transferred to the blood plasma bag and the buffy coat (BC) of the intermediate layer to the buffy coat bag. Thereafter, the erythrocyte preserving liquid in the preserving liquid bag was transferred to the blood collecting bag and added to the concentrated erythrocyte (CRC) left behind in the blood collecting bag.

Then, the blood collecting bag which contained the concentrated erythrocyte incorporated therein the added erythrocyte preserving liquid was left standing in a refrigerator at 4° C. without stirring the concentrated erythrocyte. After one week's standing in the refrigerator, the blood collecting bag was visually examined to determine whether or not the content of the bag had formed floccules. The results are shown in Table 3.

TABLE 3

Ratio of occurrence of floccules in erythrocyte after one week's standing

Number of samples: 12 each

| | Experiment 1 | | Experiment 2 | |
| --- | --- | --- | --- | --- |
| | Example 1 | Control 1 | Example 2 | Control 2 |
| Ratio of occurrence of floccules | 0/12 | 2/12 | 0/12 | 1/12 |

It is clearly noted from Table 3 that when the composites of interconnected bags of Examples 1 and 2 were used, the occurrence of floccules was not observed at all in spite of the fact that the concentrated erythrocyte were not stirred after the addition of the erythrocyte preserving liquid. In contrast, when the composites of interconnected bags of Controls 1 and 2 were used and treated in the same manner as described above, the concentrated erythrocyte incorporating the erythrocyte preserving liquid were found to have formed floccules.

The data indicate that the method of this invention for the treatment of blood which adds the erythrocyte preserving liquid upwardly from below to the concentrated erythrocyte held in the empty space 14A occupying the greater part of the empty space of the bag body of the blood collecting bag entails absolutely no occurrence of floccules and permits production of a red blood preparation of high quality.

EXAMPLE 3

A composite of interconnected bags similar to that of Example 1 was manufactured by following the procedure of Example 1, except that the partition strip of the blood collecting bag was fabricated as follows instead.

(1) Partition strip of blood collecting bag

The partition strip was disposed as shown in FIG. 3. The width of the partition strip and the position and shape of the end parts 131 were identical to those of Example 1.

(2) Empty spaces of blood collecting bag

The empty space of the shape of a strip in the blood collecting bag was so constructed that it gradually grew towards the end part from the middle of the length thereof as shown in FIG. 3. In this case, the blood collecting bag 10 was produced so that the minimum magnitude, a, of the width of the empty space 14B was 10 mm (a/f=0.15) and the maximum magnitude, b, of the width of the empty space 14B (the width of the empty space 14B in the vicinity of the end part 131) was 15 mm (1.5 a).

The inner volume of the empty space 14B of the blood collecting bag 10 was about 1.5% of the inner volume (about 455 ml) of the empty space 14A.

Experiment 1 mentioned above was performed on the composite of interconnected bags, with the erythrocyte preserving liquid introduced via the empty space 14A and the connecting part 141 to the empty space 14B and added upwardly from below to the concentrated erythrocyte in the empty space 14B of the blood collecting bag. The treatment performed by the method of this invention entailed absolutely no occurrence of floccules.

EXAMPLE 4

Composites of interconnected bags similar to those of Examples 1 and 3 were produced by following the respective procedures, except that a blood collecting bag was constructed (the partition strips disposed symmetrically right to left) as shown in FIG. 5. The widths of the partition strips and the positions and shapes of the end parts 131 were identical with those of Examples 1 and 3. The empty spaces 55B and 55C were identical with the empty space 14B of Example 1.

Experiment 1 mentioned above was performed on the composites of interconnected bags, with the erythrocyte preserving liquid introduced via the empty space 14A and the connecting member 141 to the empty space 14B and added upwardly from below to the concentrated erythrocyte in the empty space 14B of the blood collecting bag. The treatment performed by the method of this invention entailed absolutely no occurrence of floccules.

EXAMPLE 5

Composites of interconnected bags similar to those of Example 1 and 3 were produced by following respectively the procedures of Examples 1 and 3, except that blood collecting bags thereof were identical in construction with the blood collecting bag shown in FIG. 6 (the partition strips disposed symmetrically right to left). The width of the empty space 75A was 10 mm and the inner volume of the empty space 75A was about 1.6% of the total inner volume (about 456 ml) of the empty space 75B and the empty space 75B.

Experiment 1 mentioned above was performed on the composites of interconnected bags, with the erythrocyte preserving liquid introduced via the empty space 14A and the connecting part 141 to the empty space 14B and added upwardly from below to the concentrated erythrocyte in the empty space 14B of the blood collecting bag. The treatment of blood performed by the method of this invention entailed absolutely no occurrence of floccules.

EXAMPLE 6

A composite of interconnected bags constructed as shown in FIG. 1 was produced by preparing a blood collecting bag, a preserving liquid bag, and a blood plasma bag satisfying the conditions shown below and interconnecting these bags with tubes (having an inside diameter, c, of 3 mm) made of flexible polyvinyl chloride.

(1) Sheet material for bag Same as in Example 1.

(2) Partition strip in blood collecting bag Same as in Example 1.

(3) Empty spaces of blood collecting bag The four blood collecting bags 10 were manufactured so that the empty spaces 14B of the shape of a strip had a substantially fixed widths the minimum magnitude a of which were respectively 7 mm (a/f=0.109), 10 mm (a/f=0.15), 13 mm (a/f=0.194) and 16 mm (a/f=0.234).

The inner volumes of the empty spaces 14B of the blood collecting bags 10 were 0.7 to 1.8% of the inner volume (456 ml) of the empty space 14A.

EXAMPLE 7

A composite of interconnected bags constructed as shown in FIG. 1 was produced by preparing a blood collecting bag, a preserving liquid bag, and a blood plasma bag satisfying the conditions shown below and interconnecting these bags with tubes (having an inside diameter, c, of 3 mm) made of flexible polyvinyl chloride.

(1) Sheet material for bag Same as in Example 1.

(2) Partition strip in blood collecting bag

The arrangement of the partition part 13 is as shown in FIG. 3, and width of the partition part 13, a position of the end part 131 and shape were respectively the same as in Example 1.

(3) Empty spaces of blood collecting bag

A strip empty space 14B of the blood collecting bag 10 was formed so as to increase gradually from the middle portion to direction of the end part 13 as shown in FIG. 3. In this case, the minimum widths a of the empty space 14B were 7 mm (a/f=0.109), 10 mm (a/f=0.153), 13 mm (a/f=0.194) and 16 mm (a/f=0.234) and maximum width of the empty space 14B (widths of the empty space 14B at end part region) were respectively 1.25 to 1.3a, 1.5 to 1.6a and 2a and totally twelve blood collecting bags 10 were manufactured.

The inner volumes of the empty space 14B of the blood collecting bags 10 were 0.8 to 2.7% of the inner volume (about 456 ml).

CONTROL 3

A similar composite of interconnected bags to that of Example 6 was manufactured, except that a BAT bag in which a tube for discharging plasmas was connected with the upper portion of the bag body as the blood collecting bag and a tube for introducing blood and a tube for discharging erythrocyte were parallelly connected with the lower end portion of the bag body.

Each composite of interconnected bags of the Examples 6 and 7 and Control 3 were subjected to the following experiments.

EXPERIMENT 3

1. Separation rate of human false blood

Figure 13:
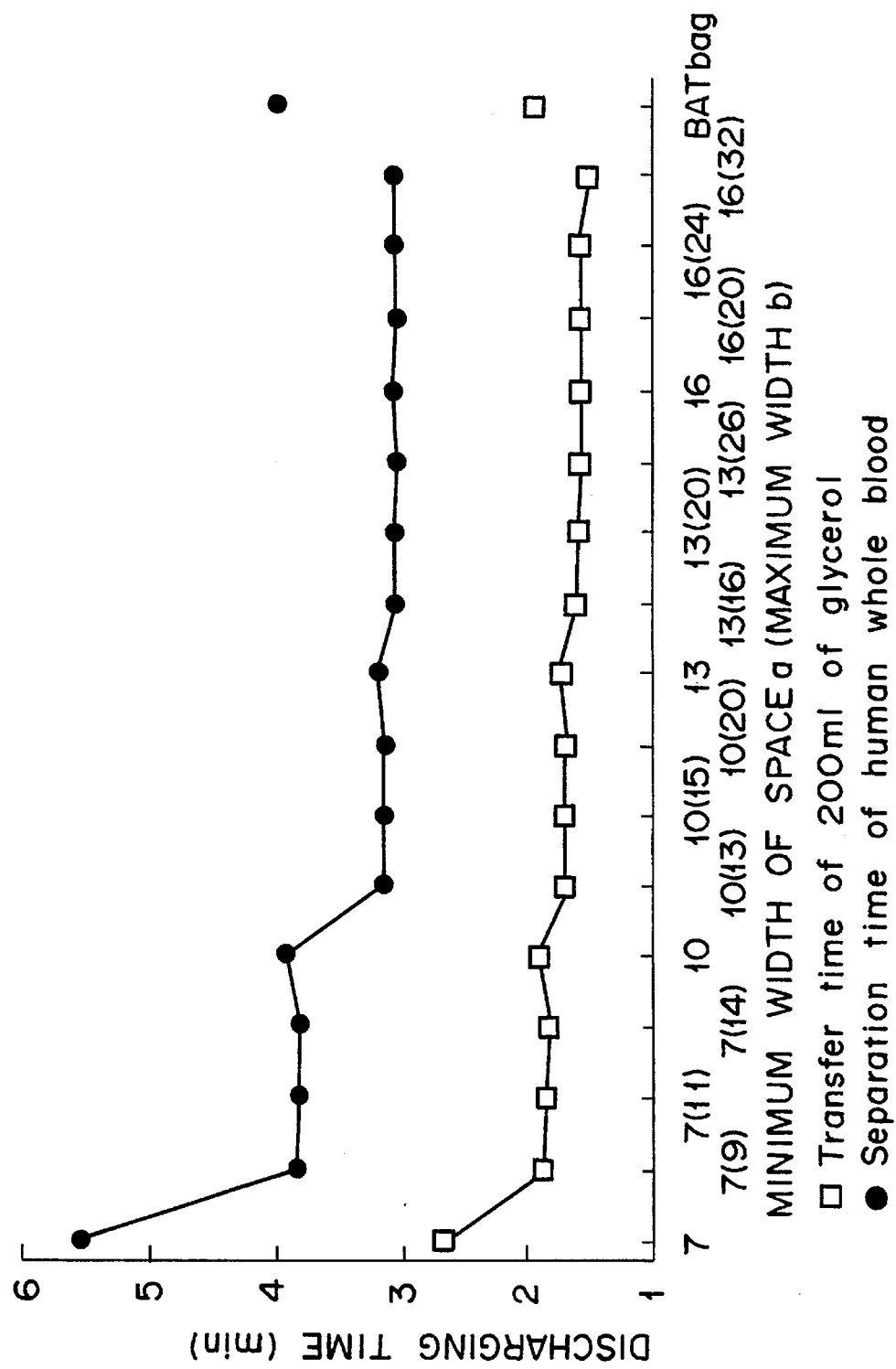
FIG. 13 is a graph showing a relationship between a width of zonal space for discharging erythrocyte in a blood collecting bag and discharging time.

75% aqueous glycerol solution (which had the same degree of viscosity to concentrated erythrocyte having 80% of Ht value) was charged into the blood collecting bag in an amount of 456 ml, then the blood collecting bag was pressed and a time requiring for transferring 200 ml of aqueous glycerol solution into an erythrocyte bag. The results are shown in FIG. 13.

Further, the oppression to each blood collecting bags in Examples 6 and 7 was carried out by using a separation stand (ME-ACS 201 produced by Terumo Kabushiki Kaisha) by hand operation, and the oppression to the blood collecting bag in Control 3 was carried out by using a specific device (OPTIPRESS produced by Baxter).

2. Separation of human whole blood

After sterilizing each composites of interconnected bags by high pressure steam, 56 ml of CPD solution (composition is shown in Table 1) was charged into the empty space 14A of the blood collecting bag as anticoagulant, 400 ml of human whole blood was collected in the empty space 14A and it was subjected to centrifugal separation by a centrifugal machine (DPR-6000 produced by IEC) at 4,000 G for 7 hours.

Then, the blood collecting bag was pressed to separate blood to three layers, and poor platelet serum (PPP) of upper layer was transfered to the plasma bag, concentrated erythrocyte (CRC) of lower layer to the erythrocyte bag and buffy coat (BC) of middle layer was removed in the blood collecting bag. The time until the completion of transfer of plasma and concentrated erythrocyte was determined so as to remain 70 ml of buffy coat in the blood collecting bag. The results are shown in FIG. 13.

Further, the oppression to each blood collecting bags in Examples 6 and 7 was carried out by using the separation stand produced by Terumo Kabushiki Kaisha by hand operation, and flow amount of discharging the plasma was controlled by pinching the tube connected with the plasma bag under recognizing by eye so as to be maintained the constant level of the buffy coat layer in the blood collecting bag. On the other hand, oppression to the blood collecting bag in Control 3 was carried out by using the specific device produced by Baxter under controlling the flow amount of plasma so as to be maintain the constant level of the buffy coat layer in the blood collecting bag under detecting by a sensor.

As being clear from FIG. 13, separated components can be discharged by using each blood collecting bags in Examples 6 and 7 by a simple operation, discharging rate does not decrease, and it becomes possible to recover the separated components in a short time.

EXPERIMENT 4

After collecting the separated components of human whole blood in Experiment 3, tubes connected with each bags are closed and cut. Then, buffy coat (BC) and concentrated erythrocyte (CRC) collected respectively to the blood collecting bag and erythrocyte bag were subjected to analysis, number of cells was determined and recovery ratio and removal ratio of each cells were obtained. Recovery ratio of erythrocyte (RBC) in concentrated erythrocyte (CRC), removal ratio of leukocyte (WBC) in concentrated erythrocyte, and recovery ratio of platelet (PLT) in buffy coat (BC) are shown respectively in FIG. 14, FIG. 15 and FIG. 16.

Figure 14:
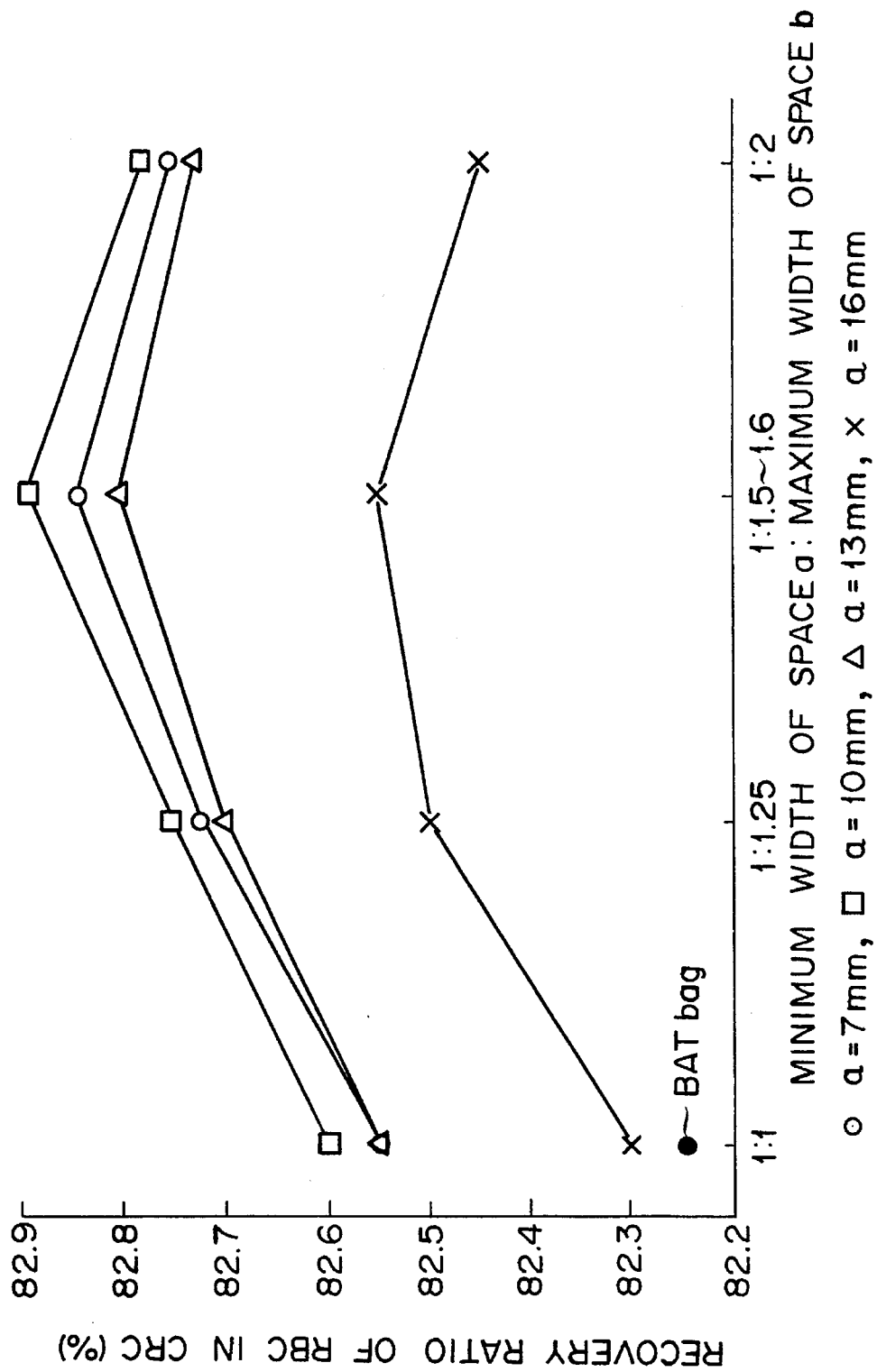
FIG. 14 is a graph showing a relationship between a ratio (a:b) of the width of zonal space for discharging erythrocyte in a blood collecting bag and a recovery ratio of erythrocyte (RBC) in concentrated erythrocyte (CRC).
Figure 15:
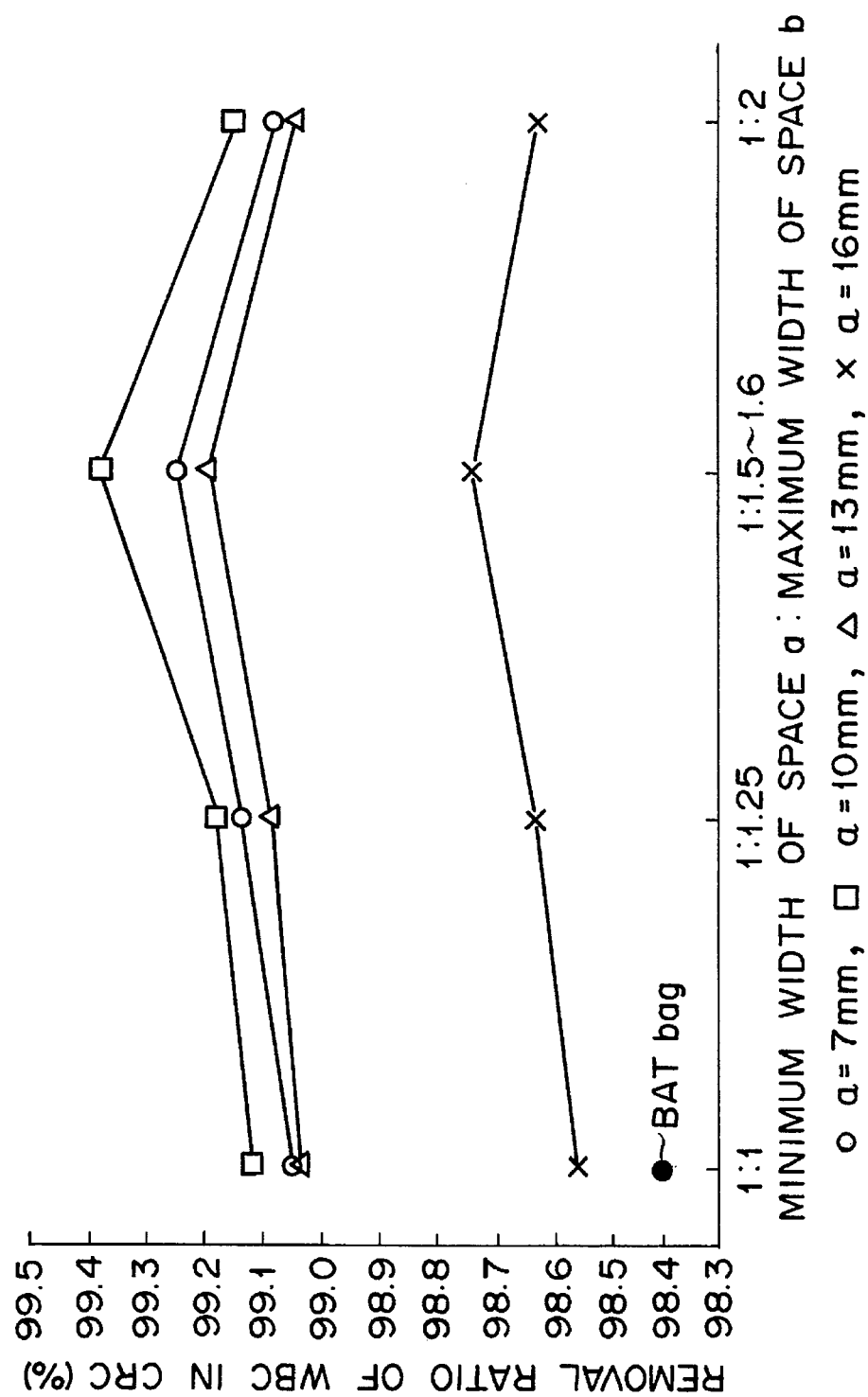
FIG. 15 is a graph showing a relationship between a ratio (a:b) of width of zonal space for discharging erythrocyte in a blood collecting bag and a removal ratio of leukocyte (WBC) in concentrated erythrocyte (CRC).
Figure 16:
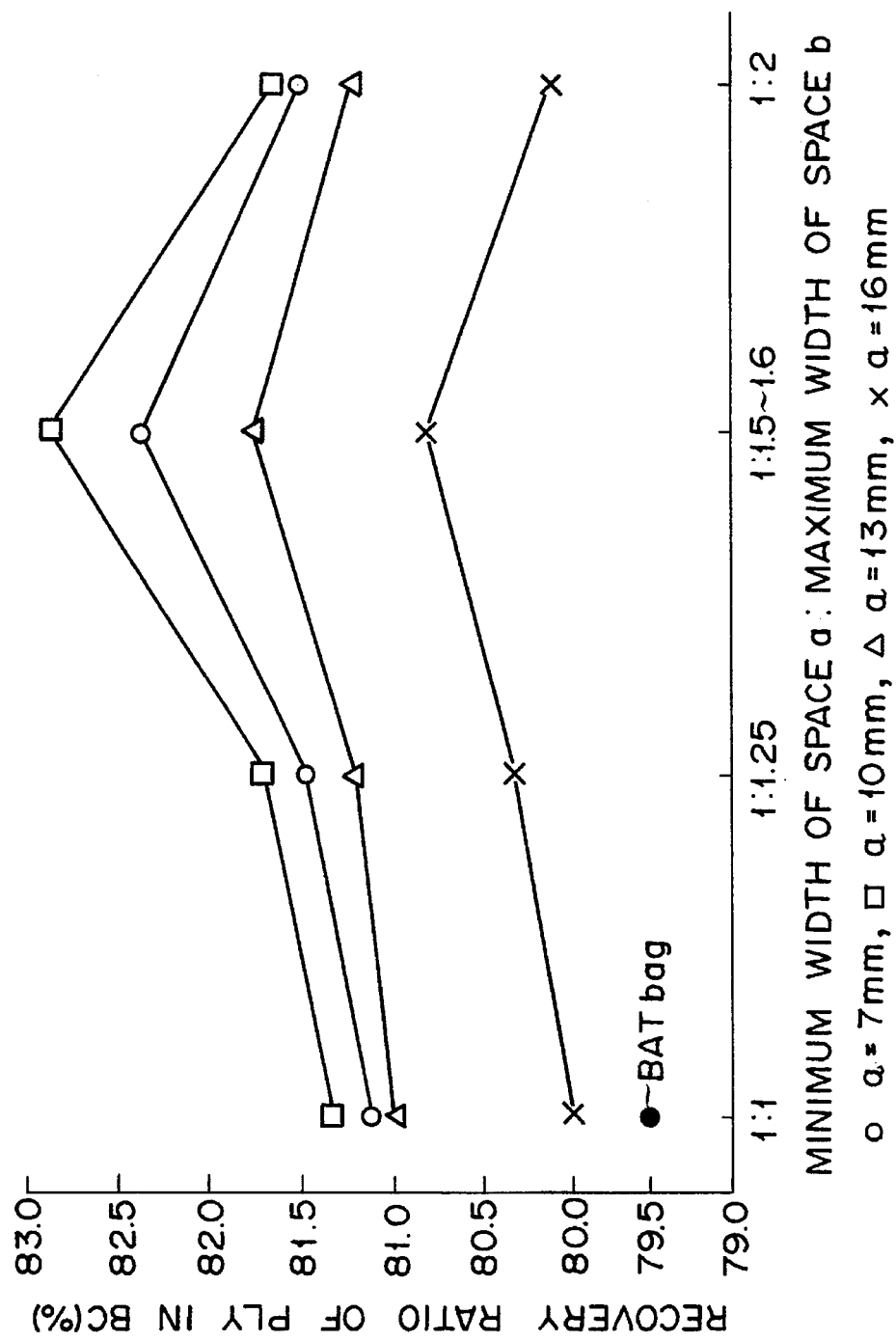
FIG. 16 is a graph showing a relationship between a ratio (a:b) of width of zonal space for discharging erythrocyte in a blood collecting bag and a recovery ratio of platelet (PLT) in a buffy coat (BC).

As being clear from each graph of FIGS. 14 to 16, according to composites of interconnected bags of Example 6 and 7, the same or more recovery ratio and removal ratio of cells are obtained as compared to Control 3 using a conventional device, although discharging of plasma and erythrocyte was carried out using a simple separation stand. Especially, enhancement of recovery ratio of erythrocyte (RBC) and removal ratio of leukocyte (WBC) can be recognized in concentrated erythrocyte (CRC).

EXAMPLE 8

A similar composite of interconnected bags to Example 6 was manufactured, except that width H of the partition strip 13 (part other than end part 131) was 3 mm, minimum width a of the strip empty space 14B was 10 mm (a/f=0.153), shape of the end part 131 of the partition strip was zero shape as shown in FIG. 1 and curvature R were 2.25 mm (0.75H), 3.0 mm (1.0H) and 4.5 mm (1.5H) respectively.

CONTROL 5

A similar composite of interconnected bags to Example 6 was manufactured, except that the shape of the end part 131 of the partition strip 13 was a half circled shape having 1.5 mm (0.5H) of the curvature.

CONTROL 6

A similar composite of interconnected bags to Example 6 was manufactured, except that the shape of the end part 131 of the partition strip 13 was cut shape.

EXPERIMENT 5

The following severe tests were carried out about each blood collecting bags in Example 8 and Controls 5 and 6.
1. Air tightness test (Seal strength test)

Air was charged into a blood collecting bag through a blood collecting needle under a gauge pressure of 1.0 kg/cm$^2$, the time until the bag breaks was determined and portion of the breakages were determined at the same time. The results are shown in Table 4. The test was carried out using each fine bags.

2. Centrifugation test

An approximately the same amount of a test liquid (it was colored easy for determination) as that of the collected blood was filled into the blood collecting bag and it was subjected to centrifugal separation in a similar centrifugal machine at 5000 G for 20 minutes. After ceitrifugation, generation of breakage of the bag was determined. The results are shown in Table 5. the tests were carried out about each six bags.

3. Pressure test

An approximately the same amount of a test liquid (it was colored easy for determination) as that of the collected blood was filled into the blood collecting bag and the blood collecting bag was pressed to increase the pressure in the bag from 1.0 kg/cm$^2$ of initial pressure, and the pressure (breakage pressure) when the bag explodes was determined. The results are shown in Table 6. The tests were carried out about each six bags.

TABLE 4

|  | Shape of end part of partition strip | breakage time (sec) | | | | | Average |
| --- | --- | --- | --- | --- | --- | --- | --- |
| Control 6 | Straight cutting | 1.2 | 1.6 | 1.5 | 1.3 | 1.4 | 1.4 |
| Control 5 | R = 0.5 H | 2.0 | 2.3 | 2.1 | 1.7 | 2.5 | 2.3 |
| Example 8 | R = 0.75 H | (7.8) | (5.6) | (6.3) | (9.1) | (5.0) | (6.7) |
| Example 8 | R = 1.0 H | (10.4) | (9.6) | (9.8) | (11.8) | (8.7) | (10.1) |
| Example 8 | R = 1.5 H | (16.2) | (7.9) | (10.8) | (14.5) | (9.7) | (11.8) |

Nemerals in parentheses show the time for breakage at the portion except the end part of the partition strip.

TABLE 5

|  | Shape of end part of partition strip | Existence of breakage of bag | | | | | | Generation ratio of breakage |
| --- | --- | --- | --- | --- | --- | --- | --- | --- |
| Control 6 | Straight cutting | O | X | O | O | O | O | 1/6 |
| Control 5 | R = 0.5 H | O | O | O | O | O | X | 1/6 |
| Example 8 | R = 0.75 H | O | O | O | O | O | O | 0/6 |
| Example 8 | R = 1.0 H | O | O | O | O | O | O | 0/6 |
| Example 8 | R = 1.5 H | O | O | O | O | O | O | 0/6 |

O: No breakage  X: breakage

TABLE 6

| | Shape of end part of partition strip | Pressure of breakage (kg/cm$^2$) | | | | | Average |
|---|---|---|---|---|---|---|---|
| Control 6 | Straight cutting | 0.8 | 1.0 | 1.2 | 1.2 | 1.1 | 1.1 |
| Control 5 | R = 0.5 H | 1.4 | 1.7 | 1.5 | 1.7 | 1.6 | 1.6 |
| Example 8 | R = 0.75 H | 2.5 | 2.4 | 2.5 | 2.1 | 2.3 | 2.3 |
| Example 8 | R = 1.0 H | 2.6 | 2.4 | 2.5 | 2.4 | 2.4 | 2.5 |
| Example 8 | R = 1.5 H | 2.2 | 2.5 | 2.3 | 2.4 | 2.4 | 2.4 |

As shown in Table 4, in the blood collecting bags in Controls 5 and 6, breakage at the end part 131 of the partition strip have generated for a relatively short time, while in the blood collecting bag in Example 8, time up to breakage is very long because the seal strength of the end part 131 is high.

Further, as shown in Table 5, in blood collecting bags in Controls 5 and 6, breakage of the bag generates by centrifugal operation, while in the blood collecting bag in Example 8, breakage of the bag does not generate by centrifugal operation.

Furthermore, as shown in Table 6, The blood collecting bag is high in breakage pressure and is difficult to be broken compared to the blood collecting bags in Controls 5 and 6.

EXAMPLE 9

The same experiments were carried out as in Experiments 3 to 5 except that the position of the end part 131 of the partition 13 to the position Z in FIG. 2 and similar bags to Examples 6 and were manufacture to obtain approximately the same results respectively.

EXAMPLE 10

A similar composite of interconnected bags to those of Examples 6 and 8 was manufactured except that the construction of the blood collecting bag is as shown in FIG. 5 (arrangement of the partition strip is symmetrical). Further, in the blood collecting bag, a position of the end parts 531 and 541 of both partition parts were a position corresponding to Y in FIG. 2, and the empty spaces 55B and 55C were similar to the empty space 14B shown in Example 6. The same experiments as Experiments 3 to 5 were carried out about each composite interconnected bags to obtain approximately the same results respectively.

As mentioned above, according to the body fluid bag of the present invention, connection of the tubes can be concentrated to one end side of the bags, so when the bags are subjected to centrifugation, it can be avoided that the bags are erromously changed in up and down position to a centrifugal cup, and when the composition interconnected bags is formed, it is easy to pile up each other, and to handle. Further, breakage of bags based on dead space in the centrifugal cup by projection of the tubes into the bag bottom does not generate. Especially, even if stress concentration generates at the end part of the partition strip during centrifugation operation, pealing and cracking do not generate at the end part because the curvature of the end part of the partition strip is large, and breakage of the bags can be avoided.

Further, the body fluid bag in accordance with the present invention can be formed only by providing the partition strip in the conventional bag, so constitution is simple, and the partition strip can be formed monolithically when the sheet materials which form bag is sealed, so it is easily manufactured even about a land and portion is formed at the end part regardless of the shape, so production cost is low.

Further, recovery of the component after centrifugal separation by simple operation using a conventional device such as a separation stand without using a special device which is complicated in operation and expensive, so discharging rate of the separated component does not occur and recovery time is short.

Furthermore, the tubes are not connected with the bottom part of the bag, so even if the recovery of the separated components is carried out using a simple device, the same or more recovery ratio and removal ratio of the separated component compared to the conventional method. Especially, when erythrocyte is recovered from whole blood, removal ratio of leukocyte (especially lymphocyte) becomes higher, so infection of hepatitis, AIDS, GVHD, etc. can be prevented in high provability by using such erythrocyte preparation.

By the method of this invention for the treatment of blood, the erythrocyte preserving liquid having a smaller specific gravity and the erythrocyte having a larger specific gravity are favorably mixed without requiring any extra work like stirring to produce an erythrocyte preparation excellent in quality and free from floccules because the erythrocyte preserving liquid is added upwardly from below instead of downwardly from above as described above. Further, since the tube for discharging the blood plasma and similar from the blood bag and the tube for transferring the erythrocyte preserving liquid into the blood bag are connected to one end part of the blood bag, the series of treatments can be performed with the one end part of the blood bag continuously kept on the upper side and, therefore, the extra work otherwise required in turning the bag upside down can be obviated. The possibility that the tubes will protrude toward the bottom part of the bag and give rise to a dead space inside the centrifugal cup during the course of centrifugal treatment and the bag will consequently sustain damage, therefore, is nil.

What is claimed is:

1. A method for the treatment of blood by the use of a blood bag comprising a pouchy bag body for storing blood, a partition strip extended inside said bag body from one end part to the other end part of said bag body, and first and second tubes connected to one end part of said bag body as opposed to each other across said partition strip, with the interior of said bag body partitioned by said partition strip into at least two empty spaces communicating with each other near the other end part of said partition strip, which method comprises centrifuging the blood collected in said blood bag with one end part of said bag body held in the upper side thereby separating the blood into an upper layer of blood plasma and a lower layer of concentrated erythrocytes, discharging said blood plasma to the exterior of said bag body via said first tube, and then transferring a erythrocyte preserving liquid having a lower specific gravity than erythrocytes to the interior of said bag body upwardly from the lower side thereof such that said erythrocyte preserving liquid ascends the mass of said concentrated erythrocytes; and wherein said erythrocytes gradually descend the mass of said erythrocyte preserving liquid such that said erythrocyte preserving liquid and said erythrocytes become mixed.

2. A method according to claim 1, wherein said other end part of said partition strip is positioned near the end part on the side opposite to the side of the end part to which said first and second tubes of said bag body are connected.

3. A method according to claim 1, wherein said other end part of said partition strip has a land part of the shape of a circle, an ellipse, or a waterdrop formed thereon.

4. A method according to claim 1, wherein at least one of the empty spaces divided by said partition strip has the shape of a strip.

5. A method according to claim 1, wherein said partition strip is obtained by adhesively joining or melting the sheet material of which said bag body is formed.

6. A method according to claim 1, wherein a third tube for introducing blood into said bag body is connected to one end part of said bag body.

7. A method according to claim 1, wherein connecting members for allowing said first and second tubes to communicate with said bag body are provided.

8. A method according to claim 7, wherein said connecting members each incorporate therein a communication impeding member adapted to obstruct communication of said bag body with said first or second tube and, on being fractured, permit said communication to be established.

9. A method according to claim 8, wherein said communication impeding members are provided outside said bag body.

10. A method according to claim 1, wherein a bag storing the erythrocyte preserving liquid is connected to said second tube.

11. A method according to claim 1, wherein another bag body is connected to said first tube.

12. A method for the treatment of blood by the use of a blood bag comprising a pouchy bag body for storing blood, a partition strip extended inside said bag body from one end part to the other end part of said bag body, and first and second tubes connected to one end part of said bag body as opposed to each other across said partition strip, with the interior of said bag body partitioned by said partition strip into at least two empty spaces communicating with each other near the other end part of said partition strip, which method comprises centrifuging the blood collected in said blood bag with one end part of said bag body held on the upper side thereby separating the blood into an upper layer of blood plasma, an intermediate layer of leukocyte, and a lower layer of concentrated erythrocytes, discharging said blood plasma and subsequently said leukocyte to the exterior of said bag body via said first tube and then transferring a erythrocyte preserving liquid having a lower specific gravity having erythrocytes to the interior of said bag body upwardly from the lower side thereof such that said erythrocyte preserving liquid ascends the mass of said concentrated erythrocytes and further wherein said erythrocytes gradually descend the mass of said erythrocyte preserving liquid such that said erythrocyte preserving liquid and said erythrocyte become mixed.

13. A method according to claim 12, wherein said other end part on said partition strip is positioned near the end part on the side opposite to the side of the end part to which said first and second tubes of said bag body are connected.

14. A method according to claim 12, wherein said other end part of said partition strip has a land part of the shape of a circle, and ellipse, or a waterdrop formed thereon.

15. A method according to claim 12, wherein at least one of the empty spaces divided by said partition strip has the shape of a strip.

16. A method according to claim 12, wherein said partition strip is obtained by adhesively joining or melting the sheet material of which said bag body is formed.

17. A method according to claim 12, wherein a third tube for introducing blood into said bag body is connected to one end part of said bag body.

18. A method according to claim 12, wherein connecting members for allowing said first and second tubes to communicate with said bag body are provided.

19. A method according to claim 18, wherein said connecting members each incorporate therein communication impeding member adapted to obstruct communication of said bag body with said first or second tube and, on being fractured, permit said communication to be established.

20. A method according to claim 19, wherein said communication impeding members are provided outside said bag body.

21. A method according to claim 12, wherein a bag storing the erythrocyte preserving liquid is connected to said second tube.

22. A method according to claim 12, wherein another bag body is connected to said first tube.

* * * * *

UNITED STATES PATENT AND TRADEMARK OFFICE
CERTIFICATE OF CORRECTION

PATENT NO. : 5,523,004
DATED : June 4, 1996
INVENTOR(S) : Nobukazu TANOKURA et al It is certified that error appears in the above-indentified patent and that said Letters Patent is hereby corrected as shown below:

In Column 8, line 12, delete "are" and insert -- arc --.

Signed and Sealed this

Twentieth Day of May, 1997

Attest:

BRUCE LEHMAN

*Attesting Officer*     Commissioner of Patents and Trademarks